(12) United States Patent
Tang et al.

(10) Patent No.: US 11,312,970 B2
(45) Date of Patent: Apr. 26, 2022

(54) COMPOSITIONS AND METHODS FOR MODULATING EXPRESSION OF NUCLEIC ACIDS

(71) Applicant: SYNGENTA PARTICIPATIONS AG, Basel (CH)

(72) Inventors: Guo-Qing Tang, Durham, NC (US); Xiang Huang, Cary, NC (US)

(73) Assignee: Syngenta Participations AG, Basel (CH)

( * ) Notice: Subject to any disclaimer, the term of this patent is extended or adjusted under 35 U.S.C. 154(b) by 272 days.

(21) Appl. No.: 15/518,592

(22) PCT Filed: Dec. 11, 2015

(86) PCT No.: PCT/US2015/065190
§ 371 (c)(1),
(2) Date: Apr. 12, 2017

(87) PCT Pub. No.: WO2016/094768
PCT Pub. Date: Jun. 16, 2016

(65) Prior Publication Data
US 2017/0283815 A1    Oct. 5, 2017

Related U.S. Application Data

(60) Provisional application No. 62/091,259, filed on Dec. 12, 2014.

(51) Int. Cl.
*C12N 15/82* (2006.01)
(52) U.S. Cl.
CPC .................. *C12N 15/8218* (2013.01)
(58) Field of Classification Search
None
See application file for complete search history.

(56) References Cited

U.S. PATENT DOCUMENTS

2014/0259222 A1    9/2014 Huang et al.

OTHER PUBLICATIONS

Axtell et al. (The Plant Cell, 2018, 30:272-284).*
Yu et al (Front Plant Sci., 2014, 5:622).*
Li et al (The Plant Cell, 2013, 25: 1507-1522).*
International Search Report received in PCT Application No. PCT/US2015/85190 dated Apr. 27, 2016.
Ossowski et al., Plant J., Feb. 2008, 53, 4, 674-690.

* cited by examiner

*Primary Examiner* — Stephen Uyeno
(74) *Attorney, Agent, or Firm* — Dale Skalla

(57) ABSTRACT

The invention relates to synthetic miRNA precursor molecules and methods for the use of the miRNA precursor molecules in modulating the expression of target polynucleotides.

1 Claim, 6 Drawing Sheets
Specification includes a Sequence Listing.

Fig. 1

>osa-MIR159b MI0001093
GGUUAUGAAGUGGAGCUCCUUUCGUUCCAAUGAAAGGUUUAUCUGAAGGGUG
AUACAGCUGCUUGUUCAUGGUUCCCACUAUUCUAUCUCAUAGGAAAAGAGAU
AGGCUUGUGGUUUGCAUGACCAAGGAGCCGAAUCAACUCCUUGCUGACCACUC
UUUGGAUUGAAGGGAGCUCUGCAUCUUGAUC SEQ ID NO:64

>zma-MIR159a MI0001809
UCGAUGCUUUGGGUUUGAAGCGGAGCUCCUAUCAUUCCAAUGAAGGGUCGUU
CCGAAGGGCUGGUUCCGCUGCUCGUUCAUGGUUCCCACUAUCCUAUCUCAUCA
UGUGUAUAUAUGUAAUCCAUGGGGGAGGGUUUCUCUCGUCUUUGAGAUAGGC
UUGUGGUUUGCAUGACCGAGGAGCUGCACCGCCCCUUGCUGGCCGCUCUUUG
GAUUGAAGGGAGCUCUGCAUCCUGAUCCACCCCUCC SEQ ID NO:65

>sbi-MIR159a MI0001572
AGCGAAGCUCCUAUCAUUCCAAUGAAGGGCCCUUUUCAUGGGUGGUUCCGCUG
CUCGUUCAUGGUUCCCACUAUCCUAUCUCAUCAUGUAUGUGUGUAUGUACUCU
AGAGGGCCCGAGAAGAGAUUCAUGUGGUCGUCAGUCUUUGAGAUAGGCUUGU
GGUUUGCAUGACCGAGGAGCUGCACCGUCCCCUUGCUGGCCGCUCUUUGGAUU
GAAGGGAGCUCUGCA SEQ ID NO:66

>tae-MIR159a MI0006170
GUGGAGCUCCUAUCAUUCCAAUGAAGGGUCUACCGGAAGGGUUUGUGCAGCU
GCUCGUUCAUGGUUCCCACUAUCCUAUCUCCAUAGAAAACGAGGAGAGAGGCC
UGUGGUUUG SEQ ID NO:67

Fig. 2

>zma-MIR159a-156
UCGAUGCUUUGGGUUUGAAGCGUGCUCAUUAUCUCCUGUCUGAAGGGUCGUU
CCGAAGGGCUGGUUCCGCUGCUCGUUCAUGGUUCCCACUAUCCUAUCUCAUCA
UGUGUAUAUAUGUAAUCCAUGGGGGAGGGUUUCUCUCGUCUUUGAGAUAGGC
UUGUGGUUUGCAUGACCGAGGAGCUGCACCGCCCCUUGCUGGCCGCUCUGAC
AGAAGAGAGUGAGCACGCAUCCUGAUCCACCCCUCC SEQ ID NO:68

22624

SEQUENCE LISTING

<160> NUMBER OF SEQ ID NOS: 68

<210> SEQ ID NO 1
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u

<400> SEQUENCE: 1
gngnnnnnnn nnnnnnnnnn nnnnn                                          25

<210> SEQ ID NO 2
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(17)
<223> OTHER INFORMATION: n is a, c, g, or u
<220> FEATURE:
<221> NAME/KEY: misc_feature
<222> LOCATION: (18)..(24)
<223> OTHER INFORMATION: Nucleotide is present or absent and when
      present is a, c, g, or u

<400> SEQUENCE: 2
unnnnnnnnn nnnnnnnnn nnnnc                                           25

<210> SEQ ID NO 3
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 3
garsgggccu acggacggug uugu                                           24

<210> SEQ ID NO 4
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 4
accacaccgu ccgggcccsm uc                                             22

<210> SEQ ID NO 5
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 5
uccgcugcyc guucaug                                                    17

<210> SEQ ID NO 6
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 6
caugaccgrg gagcugc                                                    17

<210> SEQ ID NO 7
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 7
guucccmmua ucuacuucca                                                 20

<210> SEQ ID NO 8
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 8
uggaaguagc uukkgguuug                                                 20

<210> SEQ ID NO 9
<211> LENGTH: 320
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(50)
<223> OTHER INFORMATION: Nucleotide is present or absent and when
      present is a, c, g, or u
<220> FEATURE:
<221> NAME/KEY: misc_feature
<222> LOCATION: (52)..(52)
<223> OTHER INFORMATION: n is a, c, g, or u
<220> FEATURE:
<221> NAME/KEY: misc_feature
<222> LOCATION: (54)..(68)
<223> OTHER INFORMATION: n is a, c, g, or u
<220> FEATURE:
<221> NAME/KEY: misc_feature
<222> LOCATION: (69)..(75)
<223> OTHER INFORMATION: Nucleotide is present or absent and when
      present is a, c, g, or u
<220> FEATURE:
<221> NAME/KEY: misc_feature
<222> LOCATION: (137)..(146)
<223> OTHER INFORMATION: n is a, c, g, or u
<220> FEATURE:

```
<221> NAME/KEY: misc_feature
<222> LOCATION: (147)..(186)
<223> OTHER INFORMATION: Nucleotide is present or absent and when
      present is a, c, g, or u
<220> FEATURE:
<221> NAME/KEY: misc_feature
<222> LOCATION: (247)..(262)
<223> OTHER INFORMATION: n is a, c, g, or u
<220> FEATURE:
<221> NAME/KEY: misc_feature
<222> LOCATION: (263)..(269)
<223> OTHER INFORMATION: Nucleotide is present or absent and when
      present is a, c, g, or u
<220> FEATURE:
<221> NAME/KEY: misc_feature
<222> LOCATION: (271)..(320)
<223> OTHER INFORMATION: Nucleotide is present or absent and when
      present is a, c, g, or u

<400> SEQUENCE: 9
nnnnnnnnnn nnnnnnnnnn nnnnnnnnnn nnnnnnnnnn nnnnnnnnnn gngnnnnnnn    60
nnnnnnnnnn nnnnngarsg ggccuacgga cggmguuguu ccgcugcycg uucaugguuc   120
ccmmuaucua cuuccannnn nnnnnnnnnn nnnnnnnnnn nnnnnnnnnn nnnnnnnnnn   180
nnnnnnugga aguagcuukk gguuugcaug accgrggagc ugcaccacac cguccgggcc   240
csmucunnnn nnnnnnnnnn nnnnnnnnnc nnnnnnnnnn nnnnnnnnnn nnnnnnnnnn   300
nnnnnnnnnn nnnnnnnnnn                                              320

<210> SEQ ID NO 10
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 10
ucauguuaua gaucucgucu u                                             21

<210> SEQ ID NO 11
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 11
ucauguuaua gaucucgu                                                 18

<210> SEQ ID NO 12
<211> LENGTH: 14
<212> TYPE: RNA
<213> ORGANISM: Artificial Sequence
<220> FEATURE:
<223> OTHER INFORMATION: Synthetic oligonucleotide

<400> SEQUENCE: 12
uguuauagau cucg                                                     14

<210> SEQ ID NO 13
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 13
```
ucagagagag agagagaugu c                                              21

<210> SEQ ID NO 14
<211> LENGTH: 44
<212> TYPE: RNA
<213> ORGANISM: Artificial Sequence
<220> FEATURE:
<223> OTHER INFORMATION: Synthetic oligonucleotide

<400> SEQUENCE: 14
ucauguguau auauguaauc caugggggag gguucucucg ucuu                     44

<210> SEQ ID NO 15
<211> LENGTH: 18
<212> TYPE: RNA
<213> ORGANISM: Artificial Sequence
<220> FEATURE:
<223> OTHER INFORMATION: Synthetic oligonucleotide

<400> SEQUENCE: 15
ucaucuuaua caucuccu                                                  18

<210> SEQ ID NO 16
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 16
gcguuauucg guguuugaa                                                 19

<210> SEQ ID NO 17
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 17
auccuaacac cugccauugu                                                20

<210> SEQ ID NO 18
<211> LENGTH: 220
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (87)..(96)
<223> OTHER INFORMATION: n is a, c, g, or u
<220> FEATURE:
<221> NAME/KEY: misc_feature
<222> LOCATION: (97)..(136)
<223> OTHER INFORMATION: Nucleotide is present or absent and when
      present is a, c, g, or u -continued

```
<220> FEATURE:
<221> NAME/KEY: misc_feature
<222> LOCATION: (197)..(212)
<223> OTHER INFORMATION: n is a, c, g, or u
<220> FEATURE:
<221> NAME/KEY: misc_feature
<222> LOCATION: (213)..(219)
<223> OTHER INFORMATION: Nucleotide is present or absent and when
      present is a, c, g, or u

<400> SEQUENCE: 18
gngnnnnnnn nnnnnnnnnn nnnnngarsg ggccuacgga cgguguuguu ccgcugcycg      60
uucaugguuc ccmmuaucua cuuccannnn nnnnnnnnnn nnnnnnnnnn nnnnnnnnnn     120
nnnnnnnnnn nnnnnnugga aguagcuukk gguuugcaug accgrggagc ugcaccacac     180
cguccgggcc csmucunnnn nnnnnnnnnn nnnnnnnnnc                          220

<210> SEQ ID NO 19
<211> LENGTH: 220
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (87)..(100)
<223> OTHER INFORMATION: n is a, c, g, or u
<220> FEATURE:
<221> NAME/KEY: misc_feature
<222> LOCATION: (101)..(136)
<223> OTHER INFORMATION: Nucleotide is present or absent
<220> FEATURE:
<221> NAME/KEY: misc_feature
<222> LOCATION: (197)..(212)
<223> OTHER INFORMATION: n is a, c, g, or u
<220> FEATURE:
<221> NAME/KEY: misc_feature
<222> LOCATION: (213)..(219)
<223> OTHER INFORMATION: Nucleotide is present or absent and when
      present is a, c, g, or u

<400> SEQUENCE: 19
gngnnnnnnn nnnnnnnnnn nnnnngarsg ggccuacgga cgguguuguu ccgcugcycg      60
uucaugguuc ccmmuaucua cuuccannnn nnnnnnnnnn nnnnnnnnnn nnnnnnnnnn     120
nnnnnnnnnn nnnnnnugga aguagcuukk gguuugcaug accgrggagc ugcaccacac     180
cguccgggcc csmucunnnn nnnnnnnnnn nnnnnnnnnc                          220

<210> SEQ ID NO 20
<211> LENGTH: 214
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
```

```
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (87)..(96)
<223> OTHER INFORMATION: n is a, c, g, or u
<220> FEATURE:
<221> NAME/KEY: misc_feature
<222> LOCATION: (97)..(130)
<223> OTHER INFORMATION: Nucleotide is present or absent and when
      present is a, c, g, or u
<220> FEATURE:
<221> NAME/KEY: misc_feature
<222> LOCATION: (191)..(206)
<223> OTHER INFORMATION: n is a, c, g, or u
<220> FEATURE:
<221> NAME/KEY: misc_feature
<222> LOCATION: (207)..(213)
<223> OTHER INFORMATION: Nucleotide is present or absent and when
      present is a, c, g, or u

<400> SEQUENCE: 20 gngnnnnnnnn nnnnnnnnnn nnnnngarsg ggccuacgga cgguguuguu ccgcugcycg      60
uucaugguuc ccmmuaucua cuuccannnn nnnnnnnnnn nnnnnnnnnn nnnnnnnnnn     120
nnnnnnnnnn uggaaguagc uukkgguuug caugaccgrg gagcugcacc acaccguccg     180
ggcccsmucu nnnnnnnnnn nnnnnnnnnn nnnc                                 214

<210> SEQ ID NO 21
<211> LENGTH: 191
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (87)..(96)
<223> OTHER INFORMATION: n is a, c, g, or u
<220> FEATURE:
<221> NAME/KEY: misc_feature
<222> LOCATION: (97)..(107)
<223> OTHER INFORMATION: Nucleotide is present or absent and when
      present is a, c, g, or u
<220> FEATURE:
<221> NAME/KEY: misc_feature
<222> LOCATION: (168)..(183)
<223> OTHER INFORMATION: n is a, c, g, or u
<220> FEATURE:
<221> NAME/KEY: misc_feature
<222> LOCATION: (184)..(191)
<223> OTHER INFORMATION: Nucleotide is present or absent and when
      present is a, c, g, or u

<400> SEQUENCE: 21
``` gngnnnnnnnn nnnnnnnnnn nnnnngarsg ggccuacgga cgguguuguu ccgcugcycg    60
uucauggunc ccmmuaucua cuuccannnn nnnnnnnnnn nnnnnnnugg aaguagcuuk    120
kgguuugcau gaccgrggag cugcaccaca ccguccgggc ccsmucunnn nnnnnnnnnn   180
nnnnnnnnnn c                                                         191

<210> SEQ ID NO 22
<211> LENGTH: 191
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (168)..(183)
<223> OTHER INFORMATION: n is a, c, g, or u
<220> FEATURE:
<221> NAME/KEY: misc_feature
<222> LOCATION: (184)..(190)
<223> OTHER INFORMATION: Nucleotide is present or absent and when
      present is a, c, g, or u

<400> SEQUENCE: 22 gngnnnnnnnn nnnnnnnnnn nnnnngarsg ggccuacgga cgguguuguu ccgcugcycg    60
uucauggunc ccmmuaucua cuuccaucau guuauagauc ucgucuuugg aaguagcuuk   120
kgguuugcau gaccgrggag cugcaccaca ccguccgggc ccsmucunnn nnnnnnnnn   180 nnnnnnnnnn c                                                         191

<210> SEQ ID NO 23
<211> LENGTH: 188
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (165)..(180)
<223> OTHER INFORMATION: n is a, c, g, or u
<220> FEATURE:
<221> NAME/KEY: misc_feature
<222> LOCATION: (181)..(187)
<223> OTHER INFORMATION: Nucleotide is present or absent and when
      present is a, c, g, or u

<400> SEQUENCE: 23

```
gngnnnnnnn nnnnnnnnnn nnnnngarsg ggccuacgga cgguguuguu ccgcugcycg    60
uucaugguuc ccmmuaucua cuuccaucau guuauagauc ucguuggaag uagcuukkgg   120
uuugcaugac cgrggagcug caccacaccg uccgggcccs mucunnnnnn nnnnnnnnnn   180 nnnnnnnc                                                           188
```

```
<210> SEQ ID NO 24
<211> LENGTH: 184
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (161)..(176)
<223> OTHER INFORMATION: n is a, c, g, or u
<220> FEATURE:
<221> NAME/KEY: misc_feature
<222> LOCATION: (177)..(183)
<223> OTHER INFORMATION: Nucleotide is present or absent and when
      present is a, c, g, or u

<400> SEQUENCE: 24
gngnnnnnnn nnnnnnnnnn nnnnngarsg ggccuacgga cgguguuguu ccgcugcycg    60
uucaugguuc ccmmuaucua cuuccauguu auagaucucg uggaaguagc uukkgguuug   120
caugaccgrg gagcugcacc acaccguccg ggcccsmucu nnnnnnnnnn nnnnnnnnnn   180 nnnc                                                               184
```

```
<210> SEQ ID NO 25
<211> LENGTH: 190
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (167)..(182)
<223> OTHER INFORMATION: n is a, c, g, or u
<220> FEATURE:
<221> NAME/KEY: misc_feature
<222> LOCATION: (183)..(189)
<223> OTHER INFORMATION: Nucleotide is present or absent and when
      present is a, c, g, or u
```

<400> SEQUENCE: 25

```
gngnnnnnnn nnnnnnnnnn nnnnngarsg ggccuacgga cggguuuguu ccgcugcycg    60
uucaugguuc ccmmuaucua cuuccaucag agagagagag agauguugga aguagcuukk   120
gguuugcaug accgrggagc ugcaccacac cguccgggcc csmucunnnn nnnnnnnnnn   180
nnnnnnnnnc                                                          190
```

```
<210> SEQ ID NO 26
<211> LENGTH: 214
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (191)..(206)
<223> OTHER INFORMATION: n is a, c, g, or u
<220> FEATURE:
<221> NAME/KEY: misc_feature
<222> LOCATION: (207)..(213)
<223> OTHER INFORMATION: Nucleotide is present or absent and when
      present is a, c, g, or u
```

<400> SEQUENCE: 26

```
gngnnnnnnn nnnnnnnnnn nnnnngarsg ggccuacgga cggguuuguu ccgcugcycg    60
uucaugguuc ccmmuaucua cuuccaucau guguauauau guaauccaug ggggagggguu  120
cucucgucuu uggaaguagc uukkgguuug caugaccgrg gagcugcacc acaccguccg   180
ggcccsmucu nnnnnnnnnn nnnnnnnnnn nnnc                               214
```

```
<210> SEQ ID NO 27
<211> LENGTH: 188
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (4)..(18)
<223> OTHER INFORMATION: n is a, c, g, or u
<220> FEATURE:
<221> NAME/KEY: misc_feature
<222> LOCATION: (19)..(25)
<223> OTHER INFORMATION: Nucleotide is present or absent and when
      present is a, c, g, or u
<220> FEATURE:
<221> NAME/KEY: misc_feature
<222> LOCATION: (165)..(180)
<223> OTHER INFORMATION: n is a, c, g, or u
<220> FEATURE:
<221> NAME/KEY: misc_feature
<222> LOCATION: (181)..(187)
<223> OTHER INFORMATION: Nucleotide is present or absent and when
      present is a, c, g, or u
```

<400> SEQUENCE: 27

```
gngnnnnnnn nnnnnnnnnn nnnnngarsg ggccuacgga cgguguuguu ccgcugcycg      60
uucaugguuc ccmmuaucua cuuccaucau cuuauacauc uccuuggaag uagcuukkgg     120
uuugcaugac cgrggagcug caccacaccg uccgggcccs mucunnnnnn nnnnnnnnnn    180 nnnnnnnc                                                              188
```

<210> SEQ ID NO 28
<211> LENGTH: 320
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(50)
<223> OTHER INFORMATION: Nucleotide is present or absent and when
      present is a, c, g, or u
<220> FEATURE:
<221> NAME/KEY: misc_feature
<222> LOCATION: (52)..(52)
<223> OTHER INFORMATION: n is a, c, g, or u
<220> FEATURE:
<221> NAME/KEY: misc_feature
<222> LOCATION: (54)..(68)
<223> OTHER INFORMATION: n is a, c, g, or u
<220> FEATURE:
<221> NAME/KEY: misc_feature
<222> LOCATION: (69)..(75)
<223> OTHER INFORMATION: Nucleotide is present or absent and when
      present is a, c, g, or u
<220> FEATURE:
<221> NAME/KEY: misc_feature
<222> LOCATION: (137)..(146)
<223> OTHER INFORMATION: n is a, c, g, or u
<220> FEATURE:
<221> NAME/KEY: misc_feature
<222> LOCATION: (147)..(186)
<223> OTHER INFORMATION: Nucleotide is present or absent and when
      present is a, c, g, or u
<220> FEATURE:
<221> NAME/KEY: misc_feature
<222> LOCATION: (247)..(262)
<223> OTHER INFORMATION: n is a, c, g, or u
<220> FEATURE:
<221> NAME/KEY: misc_feature
<222> LOCATION: (263)..(269)
<223> OTHER INFORMATION: Nucleotide is present or absent and when
      present is a, c, g, or u
<220> FEATURE:
<221> NAME/KEY: misc_feature
<222> LOCATION: (271)..(271)
<223> OTHER INFORMATION: n is a, c, g, or u
<220> FEATURE:
<221> NAME/KEY: misc_feature
<222> LOCATION: (272)..(320)
<223> OTHER INFORMATION: Nucleotide is present or absent and when
      present is a, c, g, or u

<400> SEQUENCE: 28

```
nnnnnnnnnn nnnnnnnnnn nnnnnnnnnn nnnnnnnnnn nnnnnnnnnn gngnnnnnnn      60
nnnnnnnnnn nnnnngarsg ggccuacgga cgguguuguu ccgcugcycg uucaugguuc    120
ccmmuaucua cuuccannnn nnnnnnnnnn nnnnnnnnnn nnnnnnnnnn nnnnnnnnnn    180
nnnnnnugga aguagcuukk gguuugcaug accgrggagc ugcaccacac cguccgggcc    240
csmucunnnn nnnnnnnnnn nnnnnnnnnc nnnnnnnnnn nnnnnnnnnn nnnnnnnnnn    300
```
nnnnnnnnnn nnnnnnnnn                                                320

<210> SEQ ID NO 29
<211> LENGTH: 314
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (2)..(50)
<223> OTHER INFORMATION: Nucleotide is present or absent and when
      present is a, c, g, or u
<220> FEATURE:
<221> NAME/KEY: misc_feature
<222> LOCATION: (52)..(52)
<223> OTHER INFORMATION: n is a, c, g, or u
<220> FEATURE:
<221> NAME/KEY: misc_feature
<222> LOCATION: (54)..(68)
<223> OTHER INFORMATION: n is a, c, g, or u
<220> FEATURE:
<221> NAME/KEY: misc_feature
<222> LOCATION: (69)..(75)
<223> OTHER INFORMATION: Nucleotide is present or absent and when
      present is a, c, g, or u
<220> FEATURE:
<221> NAME/KEY: misc_feature
<222> LOCATION: (137)..(150)
<223> OTHER INFORMATION: n is a, c, g, or u
<220> FEATURE:
<221> NAME/KEY: misc_feature
<222> LOCATION: (151)..(180)
<223> OTHER INFORMATION: Nucleotide is present or absent and when
      present is a, c, g, or u
<220> FEATURE:
<221> NAME/KEY: misc_feature
<222> LOCATION: (241)..(256)
<223> OTHER INFORMATION: n is a, c, g, or u
<220> FEATURE:
<221> NAME/KEY: misc_feature
<222> LOCATION: (257)..(263)
<223> OTHER INFORMATION: Nucleotide is present or absent and when
      present is a, c, g, or u
<220> FEATURE:
<221> NAME/KEY: misc_feature
<222> LOCATION: (265)..(265)
<223> OTHER INFORMATION: n is a, c, g, or u
<220> FEATURE:
<221> NAME/KEY: misc_feature
<222> LOCATION: (266)..(314)
<223> OTHER INFORMATION: Nucleotide is present or absent and when
      present is a, c, g, or u

<400> SEQUENCE: 29
nnnnnnnnnn nnnnnnnnnn nnnnnnnnnn nnnnnnnnnn nnnnnnnnnn gngnnnnnnn      60
nnnnnnnnnn nnnnngarsg ggccuacgga cggguuguu ccgcugcycg uucaugguuc      120
ccmmuaucua cuuccannnn nnnnnnnnnn nnnnnnnnnn nnnnnnnnnn nnnnnnnnnn      180
uggaaguagc uukkgguuug caugaccgrg gagcugcacc acaccguccg ggcccsmucu      240
nnnnnnnnnn nnnnnnnnnn nnncnnnnnn nnnnnnnnnn nnnnnnnnnn nnnnnnnnnn      300
nnnnnnnnnn nnnn                                                       314

<210> SEQ ID NO 30
<211> LENGTH: 259
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (106)..(115)
<223> OTHER INFORMATION: n is a, c, g, or u
<220> FEATURE:
<221> NAME/KEY: misc_feature
<222> LOCATION: (116)..(155)
<223> OTHER INFORMATION: Nucleotide is present or absent and when
      present is a, c, g, or u
<220> FEATURE:
<221> NAME/KEY: misc_feature
<222> LOCATION: (216)..(231)
<223> OTHER INFORMATION: n is a, c, g, or u
<220> FEATURE:
<221> NAME/KEY: misc_feature
<222> LOCATION: (232)..(238)
<223> OTHER INFORMATION: Nucleotide is present or absent and when
      present is a, c, g, or u

<400> SEQUENCE: 30
gcguuauucg guguuugaag ngnnnnnnnn nnnnnnnnnn nnnngarsgg gccuacggac      60
gguguuguuc cgcugcycgu ucauggwucc cmmuaucuac uuccannnnn nnnnnnnnnn     120
nnnnnnnnnn nnnnnnnnnn nnnnnnnnnn nnnnnuggaa guagcuukkg guuugcauga    180
ccgrggagcu gcaccacacc guccgggccc smucunnnnn nnnnnnnnnn nnnnnnnnca    240
uccuaacacc ugccauugu                                                  259

<210> SEQ ID NO 31
<211> LENGTH: 232
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (93)..(102)
<223> OTHER INFORMATION: n is a, c, g, or u
<220> FEATURE:
<221> NAME/KEY: misc_feature
<222> LOCATION: (103)..(142)
<223> OTHER INFORMATION: Nucleotide is present or absent and when
      present is a, c, g, or u
<220> FEATURE:
<221> NAME/KEY: misc_feature
<222> LOCATION: (203)..(218)
<223> OTHER INFORMATION: n is a, c, g, or u
<220> FEATURE:
<221> NAME/KEY: misc_feature
<222> LOCATION: (219)..(225)
<223> OTHER INFORMATION: Nucleotide is present or absent and when
      present is a, c, g, or u

<400> SEQUENCE: 31
uuugaagngn nnnnnnnnnn nnnnnnnnnn ngarsgggcc uacggacggu guuguuccgc    60
ugcycguuca ugguucccmm uaucuacuuc cannnnnnnn nnnnnnnnnn nnnnnnnnnn   120
nnnnnnnnnn nnnnnnnnnn nnuggaagua gcuukkgguu ugcaugaccg rggagcugca   180
ccacaccguc cgggcccsmu cunnnnnnnn nnnnnnnnnn nnnnncaucc ua           232

<210> SEQ ID NO 32
<211> LENGTH: 237
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (95)..(104)
<223> OTHER INFORMATION: n is a, c, g, or u
<220> FEATURE:
<221> NAME/KEY: misc_feature
<222> LOCATION: (105)..(144)
<223> OTHER INFORMATION: Nucleotide is present or absent and when
      present is a, c, g, or u
<220> FEATURE:
<221> NAME/KEY: misc_feature
<222> LOCATION: (205)..(220)
<223> OTHER INFORMATION: n is a, c, g, or u
<220> FEATURE:
<221> NAME/KEY: misc_feature
<222> LOCATION: (221)..(227)
<223> OTHER INFORMATION: Nucleotide is present or absent and when
      present is a, c, g, or u

<400> SEQUENCE: 32
gruuugaagn gnnnnnnnnn nnnnnnnnnn nnngarsggg ccuacggacg guguuguucc    60
gcugcycguu caugguuccc mmuaucuacu uccannnnnn nnnnnnnnnn nnnnnnnnnn   120
nnnnnnnnnn nnnnnnnnnn nnnnuggaag uagcuukkgg uuugcaugac cgrggagcug   180
caccacaccg uccgggcccs mucunnnnnn nnnnnnnnnn nnnnnnccw aguccua       237

<210> SEQ ID NO 33
<211> LENGTH: 226
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)

<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
      present is a, c, g, or u
<220> FEATURE:
<221> NAME/KEY: misc_feature
<222> LOCATION: (89)..(98)
<223> OTHER INFORMATION: n is a, c, g, or u
<220> FEATURE:
<221> NAME/KEY: misc_feature
<222> LOCATION: (99)..(138)
<223> OTHER INFORMATION: Nucleotide is present or absent and when
      present is a, c, g, or u
<220> FEATURE:
<221> NAME/KEY: misc_feature
<222> LOCATION: (199)..(214)
<223> OTHER INFORMATION: n is a, c, g, or u
<220> FEATURE:
<221> NAME/KEY: misc_feature
<222> LOCATION: (215)..(221)
<223> OTHER INFORMATION: Nucleotide is present or absent and when
      present is a, c, g, or u

<400> SEQUENCE: 33
gagngnnnnn nnnnnnnnnn nnnnnnngar sgggccuacg gacgguguug uuccgcugcy    60
cguucauggu ucccmmuauc uacuuccann nnnnnnnnnn nnnnnnnnnn nnnnnnnnnn   120
nnnnnnnnnn nnnnnnnnug gaaguagcuu kkgguuugca ugaccgrgga gcugcaccac   180
accguccggg cccsmucunn nnnnnnnnnn nnnnnnnnnn ncucua                 226

<210> SEQ ID NO 34
<211> LENGTH: 253
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (106)..(119)
<223> OTHER INFORMATION: n is a, c, g, or u
<220> FEATURE:
<221> NAME/KEY: misc_feature
<222> LOCATION: (120)..(149)
<223> OTHER INFORMATION: Nucleotide is present or absent and when
      present is a, c, g, or u
<220> FEATURE:
<221> NAME/KEY: misc_feature
<222> LOCATION: (210)..(225)
<223> OTHER INFORMATION: n is a, c, g, or u
<220> FEATURE:
<221> NAME/KEY: misc_feature
<222> LOCATION: (226)..(232)
<223> OTHER INFORMATION: Nucleotide is present or absent and when
      present is a, c, g, or u

<400> SEQUENCE: 34
gcguuauucg guguuugaag ngnnnnnnnn nnnnnnnnnn nnnngarsgg gccuacggac    60
gguguuguuc cgcugcycgu ucaugguucc cmmuaucuac uuccannnnn nnnnnnnnn    120

```
nnnnnnnnnn nnnnnnnnnn nnnnnnnnnu ggaaguagcu ukkgguuugc augaccgrgg    180
agcugcacca caccguccgg gcccsmucun nnnnnnnnnn nnnnnnnnnn nncauccuaa    240
caccugccau ugu                                                      253
```

<210> SEQ ID NO 35
<211> LENGTH: 226
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (93)..(106)
<223> OTHER INFORMATION: n is a, c, g, or u
<220> FEATURE:
<221> NAME/KEY: misc_feature
<222> LOCATION: (107)..(136)
<223> OTHER INFORMATION: Nucleotide is present or absent and when
      present is a, c, g, or u
<220> FEATURE:
<221> NAME/KEY: misc_feature
<222> LOCATION: (197)..(212)
<223> OTHER INFORMATION: n is a, c, g, or u
<220> FEATURE:
<221> NAME/KEY: misc_feature
<222> LOCATION: (213)..(219)
<223> OTHER INFORMATION: Nucleotide is present or absent and when
      present is a, c, g, or u

<400> SEQUENCE: 35

```
uuugaagngn nnnnnnnnnn nnnnnnnnnn ngarsgggcc uacggacggu guuguuccgc    60
ugcycguuca ugguucccmm uaucuacuuc cannnnnnnn nnnnnnnnnn nnnnnnnnnn    120
nnnnnnnnnn nnnnnnugga aguagcuukk gguuugcaug accgrggagc ugcaccacac    180
cguccgggcc csmucunnnn nnnnnnnnnn nnnnnnnnc auccua                   226
```

<210> SEQ ID NO 36
<211> LENGTH: 231
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (95)..(108)

<223> OTHER INFORMATION: n is a, c, g, or u
<220> FEATURE:
<221> NAME/KEY: misc_feature
<222> LOCATION: (109)..(138)
<223> OTHER INFORMATION: Nucleotide is present or absent and when
      present is a, c, g, or u
<220> FEATURE:
<221> NAME/KEY: misc_feature
<222> LOCATION: (199)..(214)
<223> OTHER INFORMATION: n is a, c, g, or u
<220> FEATURE:
<221> NAME/KEY: misc_feature
<222> LOCATION: (215)..(221)
<223> OTHER INFORMATION: Nucleotide is present or absent and when
      present is a, c, g, or u

<400> SEQUENCE: 36
gruuugaagn gnnnnnnnnn nnnnnnnnnn nnngarsggg ccuacggacg guguuguucc      60
gcugcycguu caugguuccc mmuaucuacu uccannnnnn nnnnnnnnnn nnnnnnnnnn    120
nnnnnnnnnn nnnnnnnnug gaaguagcuu kkgguuugca ugaccgrgga gcugcaccac    180
accguccggg cccsmucunn nnnnnnnnnn nnnnnnnnnn nccwaguccu a             231

<210> SEQ ID NO 37
<211> LENGTH: 220
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
      present is a, c, g, or u
<220> FEATURE:
<221> NAME/KEY: misc_feature
<222> LOCATION: (89)..(102)
<223> OTHER INFORMATION: n is a, c, g, or u
<220> FEATURE:
<221> NAME/KEY: misc_feature
<222> LOCATION: (103)..(132)
<223> OTHER INFORMATION: Nucleotide is present or absent and when
      present is a, c, g, or u
<220> FEATURE:
<221> NAME/KEY: misc_feature
<222> LOCATION: (193)..(208)
<223> OTHER INFORMATION: n is a, c, g, or u
<220> FEATURE:
<221> NAME/KEY: misc_feature
<222> LOCATION: (209)..(215)
<223> OTHER INFORMATION: Nucleotide is present or absent and when
      present is a, c, g, or u

<400> SEQUENCE: 37
gagngnnnnn nnnnnnnnnn nnnnnnngar sgggccuacg gacgguguug uuccgcugcy     60
cguucauggu ucccmmuauc uacuuccann nnnnnnnnnn nnnnnnnnnn nnnnnnnnnn    120
nnnnnnnnnn nnuggaagua gcuukkgguu ugcaugaccg rggagcugca ccacaccguc    180
cgggcccsmu cunnnnnnnn nnnnnnnnnn nnnncucua                          220

<210> SEQ ID NO 38
<211> LENGTH: 230
<212> TYPE: RNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (187)..(202)
<223> OTHER INFORMATION: n is a, c, g, or u
<220> FEATURE:
<221> NAME/KEY: misc_feature
<222> LOCATION: (203)..(209)
<223> OTHER INFORMATION: Nucleotide is present or absent and when
      present is a, c, g, or u

<400> SEQUENCE: 38
gcguuauucg guguuugaag ngnnnnnnnn nnnnnnnnnn nnnngarsgg gccuacggac    60
gguguuguuc cgcugcycgu ucaugguucc cmmuaucuac uuccaucaug uuauagaucu    120
cgucuuugga aguagcuukk gguuugcaug accgrggagc ugcaccacac cguccgggcc    180
csmucunnnn nnnnnnnnnn nnnnnnnnnc auccuaacac cugccauugu              230

<210> SEQ ID NO 39
<211> LENGTH: 227
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (184)..(199)
<223> OTHER INFORMATION: n is a, c, g, or u
<220> FEATURE:
<221> NAME/KEY: misc_feature
<222> LOCATION: (200)..(206)
<223> OTHER INFORMATION: Nucleotide is present or absent and when
      present is a, c, g, or u

<400> SEQUENCE: 39
gcguuauucg guguuugaag ngnnnnnnnn nnnnnnnnnn nnnngarsgg gccuacggac    60
gguguuguuc cgcugcycgu ucaugguucc cmmuaucuac uuccaucaug uuauagaucu    120
cguuggaagu agcuukkggu uugcaugacc grggagcugc accacaccgu ccgggcccsm    180
ucunnnnnnn nnnnnnnnnn nnnnncauc cuaacaccug ccauugu                  227

<210> SEQ ID NO 40
<211> LENGTH: 223
```

```
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (180)..(195)
<223> OTHER INFORMATION: n is a, c, g, or u
<220> FEATURE:
<221> NAME/KEY: misc_feature
<222> LOCATION: (196)..(202)
<223> OTHER INFORMATION: Nucleotide is present or absent and when
      present is a, c, g, or u

<400> SEQUENCE: 40
gcguuauucg guguuugaag ngnnnnnnnn nnnnnnnnnn nnnngarsgg gccuacggac      60 ggguguuguuc cgcugcycgu ucaugguucc cmmuaucuac uuccauguua uagaucucgu    120
ggaaguagcu ukkgguuugc augaccgrgg agcugcacca caccguccgg gcccsmucun    180
nnnnnnnnnn nnnnnnnnnn nncauccuaa caccugccau ugu                      223

<210> SEQ ID NO 41
<211> LENGTH: 230
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (187)..(202)
<223> OTHER INFORMATION: n is a, c, g, or u
<220> FEATURE:
<221> NAME/KEY: misc_feature
<222> LOCATION: (203)..(209)
<223> OTHER INFORMATION: Nucleotide is present or absent and when
      present is a, c, g, or u

<400> SEQUENCE: 41
gcguuauucg guguuugaag ngnnnnnnnn nnnnnnnnnn nnnngarsgg gccuacggac      60 ggguguuguuc cgcugcycgu ucaugguucc cmmuaucuac uuccaucaga gagagagaga   120
gaugucugga aguagcuukk gguuugcaug accgrggagc ugcaccacac cguccgggcc   180
csmucunnnn nnnnnnnnnn nnnnnnnnnc auccuaacac cugccauugu               230

<210> SEQ ID NO 42
```

-continued

```
<211> LENGTH: 253
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (210)..(225)
<223> OTHER INFORMATION: n is a, c, g, or u
<220> FEATURE:
<221> NAME/KEY: misc_feature
<222> LOCATION: (226)..(232)
<223> OTHER INFORMATION: Nucleotide is present or absent and when
      present is a, c, g, or u

<400> SEQUENCE: 42
gcguuauucg guguuugaag ngnnnnnnnn nnnnnnnnnn nnnngarsgg gccuacggac    60 ggguguuguuc cgcugcycgu ucauggguucc cmmuaucuac uuccaucaug uguauauaug   120
uaauccaugg gggagggguuc ucucgucuuu ggaaguagcu ukkgguuugc augaccgrgg   180
agcugcacca caccguccgg gcccsmucun nnnnnnnnnn nnnnnnnnnn nncauccuaa   240
caccugccau ugu    253

<210> SEQ ID NO 43
<211> LENGTH: 227
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
      present is a, c, g, or u
<220> FEATURE:
<221> NAME/KEY: misc_feature
<222> LOCATION: (184)..(199)
<223> OTHER INFORMATION: n is a, c, g, or u
<220> FEATURE:
<221> NAME/KEY: misc_feature
<222> LOCATION: (200)..(206)
<223> OTHER INFORMATION: Nucleotide is present or absent and when
      present is a, c, g, or u

<400> SEQUENCE: 43
gcguuauucg guguuugaag ngnnnnnnnn nnnnnnnnnn nnnngarsgg gccuacggac    60
gguguuguuc cgcugcycgu ucauggguucc cmmuaucuac uuccaucauc uuauacaucu   120
ccuuggaagu agcuukkggu uugcaugacc grggagcugc accaccgu ccgggcccsm   180 ucunnnnnnn nnnnnnnnnn nnnnnncauc cuaacaccug ccauugu    227
```

```
<210> SEQ ID NO 44
<211> LENGTH: 203
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (174)..(189)
<223> OTHER INFORMATION: n is a, c, g, or u
<220> FEATURE:
<221> NAME/KEY: misc_feature
<222> LOCATION: (190)..(196)
<223> OTHER INFORMATION: Nucleotide is present or absent and when
      present is a, c, g, or u

<400> SEQUENCE: 44
uuugaagngn nnnnnnnnnn nnnnnnnnnn ngarsgggcc uacggacggu guuguuccgc    60
ugcycguuca ugguucccmm uaucuacuuc caucauguua uagaucucgu cuuuggaagu   120
agcuukkggu uugcaugacc grggagcugc accacaccgu ccgggcccsm ucunnnnnnn   180
nnnnnnnnnn nnnnnncauc cua                                          203

<210> SEQ ID NO 45
<211> LENGTH: 200
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (171)..(186)
<223> OTHER INFORMATION: n is a, c, g, or u
<220> FEATURE:
<221> NAME/KEY: misc_feature
<222> LOCATION: (187)..(193)
<223> OTHER INFORMATION: Nucleotide is present or absent and when
      present is a, c, g, or u

<400> SEQUENCE: 45
uuugaagngn nnnnnnnnnn nnnnnnnnnn ngarsgggcc uacggacggu guuguuccgc    60
ugcycguuca ugguucccmm uaucuacuuc caucauguua uagaucucgu uggaaguagc   120
uukkgguuug caugaccgrg gagcugcacc acaccguccg ggcccsmucu nnnnnnnnnn   180
```
nnnnnnnnnn nnncauccua                                                    200

<210> SEQ ID NO 46
<211> LENGTH: 196
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (167)..(182)
<223> OTHER INFORMATION: n is a, c, g, or u
<220> FEATURE:
<221> NAME/KEY: misc_feature
<222> LOCATION: (183)..(189)
<223> OTHER INFORMATION: Nucleotide is present or absent and when
      present is a, c, g, or u

<400> SEQUENCE: 46
uuugaagngn nnnnnnnnnn nnnnnnnnnn ngarsgggcc uacggacggu guuguuccgc         60
ugcycguuca agguucccmm uaucuacuuc cauguuauag aucucgugga aguagcuukk        120
gguuugcaug accgrggagc ugcaccacac cguccgggcc csmucunnnn nnnnnnnnnn        180
nnnnnnnnnc auccua                                                       196

<210> SEQ ID NO 47
<211> LENGTH: 203
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (174)..(189)
<223> OTHER INFORMATION: n is a, c, g, or u
<220> FEATURE:
<221> NAME/KEY: misc_feature
<222> LOCATION: (190)..(196)
<223> OTHER INFORMATION: Nucleotide is present or absent and when
      present is a, c, g, or u

<400> SEQUENCE: 47
uuugaagngn nnnnnnnnnn nnnnnnnnnn ngarsgggcc uacggacggu guuguuccgc         60
ugcycguuca agguucccmm uaucuacuuc caucagagag agagagagau gucuggaagu        120
agcuukkggu uugcaugacc grggagcugc accacaccgu ccgggcccsm ucunnnnnnn        180
nnnnnnnnnn nnnnnncauc cua                                              203

<210> SEQ ID NO 48
<211> LENGTH: 226
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (197)..(212)
<223> OTHER INFORMATION: n is a, c, g, or u
<220> FEATURE:
<221> NAME/KEY: misc_feature
<222> LOCATION: (213)..(219)
<223> OTHER INFORMATION: Nucleotide is present or absent and when
      present is a, c, g, or u

<400> SEQUENCE: 48
uuugaagngn nnnnnnnnnn nnnnnnnnnn ngarsgggcc uacggacggu guuguuccgc       60
ugcycguuca ugguucccmm uaucuacuuc caucaugugu auauauguaa uccauggggg      120 agguucucu cgucuuugga aguagcuukk gguuugcaug accgrggagc ugcaccacac       180
cguccgggcc csmucunnnn nnnnnnnnnn nnnnnnnnnc auccua                    226

<210> SEQ ID NO 49
<211> LENGTH: 200
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (10)..(24)
<223> OTHER INFORMATION: n is a, c, g, or u
<220> FEATURE:
<221> NAME/KEY: misc_feature
<222> LOCATION: (25)..(31)
<223> OTHER INFORMATION: Nucleotide is present or absent and when
      present is a, c, g, or u
<220> FEATURE:
<221> NAME/KEY: misc_feature
<222> LOCATION: (171)..(186)
<223> OTHER INFORMATION: n is a, c, g, or u
<220> FEATURE:
<221> NAME/KEY: misc_feature
<222> LOCATION: (187)..(193)
<223> OTHER INFORMATION: Nucleotide is present or absent and when
      present is a, c, g, or u

<400> SEQUENCE: 49
uuugaagngn nnnnnnnnnn nnnnnnnnnn ngarsgggcc uacggacggu guuguuccgc       60
ugcycguuca ugguucccmm uaucuacuuc caucaucuua uacaucuccu uggaaguagc     120

```
uukkgguuug caugaccgrg gagcugcacc acaccguccg ggcccsmucu nnnnnnnnnn    180
nnnnnnnnnn nnncauccua                                                200
```

<210> SEQ ID NO 50
<211> LENGTH: 208
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (176)..(191)
<223> OTHER INFORMATION: n is a, c, g, or u
<220> FEATURE:
<221> NAME/KEY: misc_feature
<222> LOCATION: (192)..(198)
<223> OTHER INFORMATION: Nucleotide is present or absent and when
      present is a, c, g, or u

<400> SEQUENCE: 50

```
gruugaagn gnnnnnnnnn nnnnnnnnnn nnngarsggg ccuacggacg guguuguucc     60
gcugcycguu caugguuccc mmuaucuacu uccaucaugu uauagaucuc gucuuuggaa   120
guagcuukkg guuugcauga ccgrggagcu gcaccacacc guccgggccc smucunnnnn   180
nnnnnnnnnn nnnnnnnncc waguccua                                      208
```

<210> SEQ ID NO 51
<211> LENGTH: 205
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (173)..(188)
<223> OTHER INFORMATION: n is a, c, g, or u
<220> FEATURE:
<221> NAME/KEY: misc_feature
<222> LOCATION: (189)..(195)
<223> OTHER INFORMATION: Nucleotide is present or absent and when
      present is a, c, g, or u

<400> SEQUENCE: 51

```
gruugaagn gnnnnnnnnn nnnnnnnnnn nnngarsggg ccuacggacg guguuguucc     60
gcugcycguu caugguuccc mmuaucuacu uccaucaugu uauagaucuc guuggaagua   120
```

```
gcuukkgguu ugcaugaccg rggagcugca ccacaccguc cgggcccsmu cunnnnnnnn    180
nnnnnnnnnn nnnnnccwag uccua                                          205
```

<210> SEQ ID NO 52
<211> LENGTH: 201
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (169)..(184)
<223> OTHER INFORMATION: n is a, c, g, or u
<220> FEATURE:
<221> NAME/KEY: misc_feature
<222> LOCATION: (185)..(191)
<223> OTHER INFORMATION: Nucleotide is present or absent and when
      present is a, c, g, or u

<400> SEQUENCE: 52

```
gruuugaagn gnnnnnnnnn nnnnnnnnnn nnngarsggg ccuacggacg guguuguucc    60
gcugcycguu caugguuccc mmuaucuacu uccauguuau agaucucgug gaaguagcuu   120
kkgguuugca ugaccgrgga gcugcaccac accguccggg cccsmucunn nnnnnnnnn    180 nnnnnnnnnn nccwaguccu a                                             201
```

<210> SEQ ID NO 53
<211> LENGTH: 208
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (176)..(191)
<223> OTHER INFORMATION: n is a, c, g, or u
<220> FEATURE:
<221> NAME/KEY: misc_feature
<222> LOCATION: (192)..(198)
<223> OTHER INFORMATION: Nucleotide is present or absent and when
      present is a, c, g, or u

<400> SEQUENCE: 53

```
gruuugaagn gnnnnnnnnn nnnnnnnnnn nnngarsggg ccuacggacg guguuguucc    60
```

```
gcugcycguu cauggruuccc mmuaucuacu uccaucagag agagagagag augucuggaa    120
guagcuukkg guuugcauga ccgrggagcu gcaccacacc guccgggccc smucunnnnn    180
nnnnnnnnnn nnnnnnnncc waguccua                                       208

<210> SEQ ID NO 54
<211> LENGTH: 231
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (199)..(214)
<223> OTHER INFORMATION: n is a, c, g, or u
<220> FEATURE:
<221> NAME/KEY: misc_feature
<222> LOCATION: (215)..(221)
<223> OTHER INFORMATION: Nucleotide is present or absent and when
      present is a, c, g, or u

<400> SEQUENCE: 54
gruuugaagn gnnnnnnnnn nnnnnnnnnn nnngarsggg ccuacggacg guguuguucc    60
gcugcycguu cauggruuccc mmuaucuacu uccaucaugu guauauaugu aauccauggg   120 ggagggruucu cucgucuuug gaaguagcuu kkgguuugca ugaccgrgga gcugcaccac   180
accguccggg cccsmucunn nnnnnnnnnn nnnnnnnnnn nccwaguccu a             231

<210> SEQ ID NO 55
<211> LENGTH: 205
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (12)..(26)
<223> OTHER INFORMATION: n is a, c, g, or u
<220> FEATURE:
<221> NAME/KEY: misc_feature
<222> LOCATION: (27)..(33)
<223> OTHER INFORMATION: Nucleotide is present or absent and when
      present is a, c, g, or u
<220> FEATURE:
<221> NAME/KEY: misc_feature
<222> LOCATION: (173)..(188)
<223> OTHER INFORMATION: n is a, c, g, or u
<220> FEATURE:
<221> NAME/KEY: misc_feature
<222> LOCATION: (189)..(195)
<223> OTHER INFORMATION: Nucleotide is present or absent and when
      present is a, c, g, or u

<400> SEQUENCE: 55
gruuugaagn gnnnnnnnnn nnnnnnnnnn nnngarsggg ccuacggacg guguuguucc    60
```

```
gcugcycguu caugguuccc mmuaucuacu uccaucaucu uauacaucuc cuuggaagua    120
gcuukkgguu ugcaugaccg rggagcugca ccacaccguc cgggcccsmu cunnnnnnnn    180
nnnnnnnnnn nnnnccwag uccua                                          205
```

<210> SEQ ID NO 56
<211> LENGTH: 197
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
    present is a, c, g, or u
<220> FEATURE:
<221> NAME/KEY: misc_feature
<222> LOCATION: (170)..(185)
<223> OTHER INFORMATION: n is a, c, g, or u
<220> FEATURE:
<221> NAME/KEY: misc_feature
<222> LOCATION: (186)..(192)
<223> OTHER INFORMATION: Nucleotide is present or absent and when
    present is a, c, g, or u

<400> SEQUENCE: 56

```
gagngnnnnn nnnnnnnnnn nnnnnnngar sgggccuacg gacgguguug uuccgcugcy    60
cguucauggu ucccmmuauc uacuuccauc auguuauaga ucucgucuuu ggaaguagcu    120
ukkgguuugc augaccgrgg agcugcacca caccguccgg gcccsmucun nnnnnnnnnn    180
nnnnnnnnnn nncucua                                                  197
```

<210> SEQ ID NO 57
<211> LENGTH: 194
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
    present is a, c, g, or u
<220> FEATURE:
<221> NAME/KEY: misc_feature
<222> LOCATION: (167)..(182)
<223> OTHER INFORMATION: n is a, c, g, or u
<220> FEATURE:
<221> NAME/KEY: misc_feature
<222> LOCATION: (183)..(189)
<223> OTHER INFORMATION: Nucleotide is present or absent and when
    present is a, c, g, or u

<400> SEQUENCE: 57

```
gagngnnnnn nnnnnnnnnn nnnnnnngar sgggccuacg gacgguguug uuccgcugcy    60
cguucauggu ucccmmuauc uacuuccauc auguuauaga ucucguugga aguagcuukk   120
gguuugcaug accgrggagc ugcaccacac cguccgggcc csmucunnnn nnnnnnnnnn   180
nnnnnnnnnc ucua                                                    194

<210> SEQ ID NO 58
<211> LENGTH: 190
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
      present is a, c, g, or u
<220> FEATURE:
<221> NAME/KEY: misc_feature
<222> LOCATION: (163)..(178)
<223> OTHER INFORMATION: n is a, c, g, or u
<220> FEATURE:
<221> NAME/KEY: misc_feature
<222> LOCATION: (179)..(185)
<223> OTHER INFORMATION: Nucleotide is present or absent and when
      present is a, c, g, or u

<400> SEQUENCE: 58
gagngnnnnn nnnnnnnnnn nnnnnnngar sgggccuacg gacgguguug uuccgcugcy    60
cguucauggu ucccmmuauc uacuuccaug uuauagaucu cguggaagua gcuukkgguu   120
ugcaugaccg rggagcugca ccacaccguc cgggcccsmu cunnnnnnnn nnnnnnnnnn   180 nnnnncucua                                                         190

<210> SEQ ID NO 59
<211> LENGTH: 197
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
      present is a, c, g, or u
<220> FEATURE:
<221> NAME/KEY: misc_feature
<222> LOCATION: (170)..(185)
<223> OTHER INFORMATION: n is a, c, g, or u
<220> FEATURE:
<221> NAME/KEY: misc_feature
<222> LOCATION: (186)..(192)
<223> OTHER INFORMATION: Nucleotide is present or absent and when
      present is a, c, g, or u

<400> SEQUENCE: 59
```

```
gagngnnnnn nnnnnnnnnn nnnnnnngar sgggccuacg dacgguguug uuccgcugcy    60
cguucauggu ucccmmuauc uacuuccauc agagagagag agagaugucu ggaaguagcu   120
ukkgguuugc augaccgrgg agcugcacca caccguccgg gcccsmucun nnnnnnnnnn   180
nnnnnnnnnn nncucua                                                  197
```

<210> SEQ ID NO 60
<211> LENGTH: 220
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
    present is a, c, g, or u
<220> FEATURE:
<221> NAME/KEY: misc_feature
<222> LOCATION: (193)..(208)
<223> OTHER INFORMATION: n is a, c, g, or u
<220> FEATURE:
<221> NAME/KEY: misc_feature
<222> LOCATION: (209)..(215)
<223> OTHER INFORMATION: Nucleotide is present or absent and when
    present is a, c, g, or u

<400> SEQUENCE: 60

```
gagngnnnnn nnnnnnnnnn nnnnnnngar sgggccuacg gacgguguug uuccgcugcy    60
cguucauggu ucccmmuauc uacuuccauc auguguauau auguaaucca ugggggaggg   120
uucucucguc uuuggaagua gcuukkgguu ugcaugaccg rggagcugca ccacaccguc   180
cgggcccsmu cunnnnnnnn nnnnnnnnnn nnnnncucua                         220
```

<210> SEQ ID NO 61
<211> LENGTH: 194
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(20)
<223> OTHER INFORMATION: n is a, c, g, or u
<220> FEATURE:
<221> NAME/KEY: misc_feature
<222> LOCATION: (21)..(27)
<223> OTHER INFORMATION: Nucleotide is present or absent and when
    present is a, c, g, or u
<220> FEATURE:
<221> NAME/KEY: misc_feature
<222> LOCATION: (167)..(182)
<223> OTHER INFORMATION: n is a, c, g, or u
<220> FEATURE:
<221> NAME/KEY: misc_feature
<222> LOCATION: (183)..(189)
<223> OTHER INFORMATION: Nucleotide is present or absent and when
    present is a, c, g, or u

<400> SEQUENCE: 61
gagngnnnnn nnnnnnnnnn nnnnnnngar sgggccuacg gacgguguug uuccgcugcy    60
cguucauggu ucccmmuauc uacuuccauc aucuuauaca ucuccuugga aguagcuukk   120
gguuugcaug accgrggagc ugcaccacac cguccgggcc csmucunnnn nnnnnnnnnn   180
nnnnnnnnnc ucua                                                    194

<210> SEQ ID NO 62
<211> LENGTH: 230
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or u
<220> FEATURE:
<221> NAME/KEY: misc_feature
<222> LOCATION: (23)..(37)
<223> OTHER INFORMATION: n is a, c, g, or u
<220> FEATURE:
<221> NAME/KEY: misc_feature
<222> LOCATION: (38)..(44)
<223> OTHER INFORMATION: Nucleotide is present or absent and when
    present is a, c, g, or u
<220> FEATURE:
<221> NAME/KEY: misc_feature
<222> LOCATION: (187)..(202)
<223> OTHER INFORMATION: n is a, c, g, or u
<220> FEATURE:
<221> NAME/KEY: misc_feature
<222> LOCATION: (203)..(209)
<223> OTHER INFORMATION: Nucleotide is present or absent and when
    present is a, c, g, or u

<400> SEQUENCE: 62
gcguuauucg guguuugaag ngnnnnnnnn nnnnnnnnnn nnnngaaggg gccuacggac    60
gguguuguuc cgcugcucgu ucaugguucc ccauaucuac uuccaucaug uuauagaucu   120
cgucuuugga aguagcuuug gguuugcaug accgaggagc ugcaccacac cguccgggcc   180
cgcucunnnn nnnnnnnnnn nnnnnnnnnc auccuaacac cugccauugu             230

<210> SEQ ID NO 63
<211> LENGTH: 224
<212> TYPE: RNA
<213> ORGANISM: Artificial Sequence
<220> FEATURE:
<223> OTHER INFORMATION: Synthetic oligonucleotide

<400> SEQUENCE: 63
gcguuauucg guguuugaag cgugcucauu aucuccuguc ugaaggggcc uacggacggu    60
guuguuccgc ugcucguuca ugguucccca uaucuacuuc caucauguua uagaucucgu   120
cuuuggaagu agcuuggggu uugcaugacc gaggagcugc accaccgu ccgggcccgc    180 ucgacagaa gagagugagc acgcauccua acaccugcca uugu                    224

<210> SEQ ID NO 64
<211> LENGTH: 188
<212> TYPE: RNA
<213> ORGANISM: Oryza sativa

<400> SEQUENCE: 64
gguuaugaag uggagcuccu uucguuccaa ugaaagguuu aucugaaggg ugauacagcu    60
gcuuguucau gguucccacu auucuaucuc auaggaaaag agauaggcuu gugguuugca   120

```
ugaccaagga gccgaaucaa cuccuugcug accacucuuu ggauugaagg gagcucugca    180
ucuugauc                                                              188

<210> SEQ ID NO 65
<211> LENGTH: 246
<212> TYPE: RNA
<213> ORGANISM: Sorghum vulgare

<400> SEQUENCE: 65
ucgaugcuuu ggguuugaag cggagcuccu aucauuccaa ugaagggucg uuccgaaggg     60
cugguuccgc ugcucguuca ugguucccac uaccuaucu caucaugugu auauauguaa    120
uccauggggg agguuucuc ucgucuuuga gauaggcuug ugguuugcau gaccgaggag    180
cugcaccgcc cccuugcugg ccgcucuuug gauugaaggg agcucugcau ccugauccac    240
cccucc                                                               246

<210> SEQ ID NO 66
<211> LENGTH: 226
<212> TYPE: RNA
<213> ORGANISM: Triticum aestivum

<400> SEQUENCE: 66
agcgaagcuc cuaucauucc aaugaagggc ccuuuucaug ggugguuccg cugcucguuc     60
augguuccca cuaccuauc ucaucaugua ugugguaug uacucuagag ggcccgagaa    120
gagauucaug uggucgucag ucuuugagau aggcuugugg uuugcaugac cgaggagcug    180
caccgucccc uugcuggccg cucuuuggau ugaagggagc ucugca                   226

<210> SEQ ID NO 67
<211> LENGTH: 114
<212> TYPE: RNA
<213> ORGANISM: Zea mays

<400> SEQUENCE: 67
guggagcucc uaucauucca augaaggguc uaccggaagg guuugugcag cugcucguuc     60
augguuccca cuaccuauc uccauagaaa acgaggagag aggccugugg uuug          114

<210> SEQ ID NO 68
<211> LENGTH: 246
<212> TYPE: RNA
<213> ORGANISM: Artificial Sequence
<220> FEATURE:
<223> OTHER INFORMATION: chimeric zma-MIR159a-miR156 sequence

<400> SEQUENCE: 68
ucgaugcuuu ggguuugaag cgugcucauu aucuccuguc ugaagggucg uuccgaaggg     60
cugguuccgc ugcucguuca ugguucccac uaccuaucu caucaugugu auauauguaa    120
uccauggggg agguuucuc ucgucuuuga gauaggcuug ugguuugcau gaccgaggag    180
cugcaccgcc cccuugcugg ccgcucugac agaagagagu gagcacgcau ccugauccac    240
cccucc                                                               246
```

COMPOSITIONS AND METHODS FOR MODULATING EXPRESSION OF NUCLEIC ACIDS

RELATED APPLICATION INFORMATION

This application is a 371 of International Application No. PCT/US2015/065190, filed Dec. 11, 2015, which claims priority to U.S. Provisional Application No. 62/091,259, filed Dec. 12, 2014, the entire contents of which are incorporated herein by reference herein.

STATEMENT REGARDING ELECTRONIC FILING OF A SEQUENCE LISTING

A Sequence Listing in ASCII text format, submitted under 37 C.F.R. § 1.821, entitled 80275-US-REG-ORG P-1 ST25.txt, 3,072 bytes in size, generated on Jul. 23, 2019 and filed via EFS-Web, is provided in lieu of a paper copy. This Sequence Listing is hereby incorporated herein by reference into the specification for its disclosures.

FIELD OF THE INVENTION

The invention relates to synthetic miRNA precursor molecules and methods for their use in modulating nucleic acid expression in plants.

BACKGROUND

MicroRNAs (miRNAs) are non-protein coding RNAs, generally of between about 17 to about 25 nucleotides (commonly about 20-24 nucleotides in plants). miRNAs direct cleavage in trans of target transcripts, regulating the expression of genes involved in various pathways (Bartel, *Cell*, 116:281-297 (2004); Zhang et al. *Dev. Biol.* 289:3-16 (2006)). miRNAs have been shown to be involved in different aspects of plant growth and development as well as in signal transduction and protein degradation. In addition, growing evidence indicates that small endogenous RNAs including miRNAs may also be involved in biotic stress responses such as parasite attack. Since the first miRNAs were discovered in plants (Reinhart et al. *Genes Dev.* 16:1616-1626 (2002), Park et al. *Curr. Biol.* 12:1484-1495 (2002)), many hundreds have been identified. Further, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database ("miRBase," microrna.sangerac.uk/sequences). miRNAs are also described in U.S. Patent Publications 2005/0120415 and 2005/144669A1, the entire contents of which are incorporated by reference herein.

Genes encoding miRNAs yield primary miRNAs ("pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nucleotides (referred to as precursor miRNAs (pre-miRNAs)) by the RNaseIII enzyme Drosha and its cofactor DGCR8/Pasha. The pre-miRNA is then exported to the cytoplasm, where it is further processed by another RNaseIII enzyme, Dicer, releasing a miRNA (guide strand)/miRNA* (passenger or carrier strand) duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel. *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim. *Nature Rev. Mol. Cell Biol.* 6:376-385 (2005).

Since shortly after the discovery of miRNAs, researchers began to utilize natural endogenous precursor miRNAs (pre-MIR) for delivery of sequence-specific RNAi in which a sequence specific RNAi (miRNA) of interest is exchanged for the natural miRNA guide sequence in the endogenous precursor. However, this approach of using endogenous precursors for miRNA delivery has limitations. For instance, insertion into a genome of an artificial miRNA precursor sequence that is driven by a strong promoter may result in interference with the processing of the original endogenous precursor. As a consequence, unintended phenotypic outcomes can occur. Accordingly, new designs for delivering sequence specific RNAi are needed.

SUMMARY OF THE INVENTION

The present invention is based, in part, on the development of a synthetic miRNA precursor molecule that is processed in plants by Dicer-like1 (DCL-1) to produce a miRNA guide strand that targets nucleic acids of interest in planta. The precursor of this invention provides a scaffold into which any guide strand can be placed for expression.

In one aspect, a synthetic miRNA precursor (nucleic acid) molecule is provided comprising the following structure 5' to 3':

A-B-C-D-E-F, wherein

A is a nucleotide sequence that is optionally present and when present comprises a first strand and a second strand each of which independently comprise 1 to 22 nucleotides;

B is a nucleotide sequence comprising a first strand and a second strand, wherein the first strand comprises a miRNA passenger strand having a nucleotide sequence of $GNGN_{15-22}$ (SEQ ID NO:1) and the second strand comprises a miRNA guide strand having the nucleotide sequence of $UN_{16-23}C$ (SEQ ID NO:2) and the passenger strand and the guide strand form a double stranded sequence having three mismatches.

C is a nucleotide sequence comprising a first strand and a second strand, wherein the first strand comprises a nucleotide sequence of GA[A/G][G/C]GGGCCUACGGACGGU-GUUGU (SEQ ID NO:3), and the second strand comprises a nucleotide sequence of ACCACACCGUCCGGGCCC[G/C][C/A]UC (SEQ ID NO:4), and the first strand and second strand form a double stranded sequence comprising two to four mismatches or bulges, or any combination thereof;

D is a nucleotide sequence comprising a first strand and a second strand, wherein the first strand comprises a nucleotide sequence of UCCGCUGC[U/C]CGUUCAUG (SEQ ID NO:5), and the second strand comprises a nucleotide sequence of CAUGACCG[A/G]GGAGCUGC (SEQ ID NO:6) and the first strand and second strand form a double stranded sequence comprising two to four mismatches;

E is a nucleotide sequence comprising a first strand and a second strand, wherein the first strand comprises a nucleotide sequence of GUUCCC[C/A][A/C]UAUCUACUUCCA (SEQ ID NO:7), and the second strand comprises a nucleotide sequence of UGGAAGUAGCUU[U/G][G/U]GGUUUG (SEQ ID NO:8) and the first strand and second strand form a double stranded sequence comprising two mismatches; and F is a sequence comprising a length of 10 to 50 nucleotides and forming a loop. In some aspects the invention provides a synthetic miRNA precursor molecule comprising, consisting essentially of, or consisting of the nucleotide sequence of SEQ ID NO:9.

In another aspect, the present invention provides a synthetic miRNA precursor molecule comprising, consisting essentially of, or consisting of the nucleotide sequence of SEQ ID NO:9 or a nucleotide sequence listed in Table 1.

In some aspects, the miRNA guide strand of the synthetic miRNA precursor molecule can be about 60% to about 100% complementary to a target polynucleotide or target gene from a plant.

In further aspects, a method of modulating the expression of a target polynucleotide in a plant of interest is provided, the method comprising: introducing into a plant or plant part a synthetic miRNA precursor molecule of the invention, optionally wherein the synthetic miRNA precursor molecule of the invention can be comprised in a recombinant nucleic acid, an expression cassette or a vector, thereby modulating the expression of a target polynucleotide or a target gene in said plant or plant part.

In addition aspects, a method of modulating the expression of a target polynucleotide or a target gene in a plant or plant part is provided, the method comprising: introducing into a plant cell a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector to produce a transgenic plant cell; and regenerating a plant or plant part from said plant cell, thereby modulating the expression of a target polynucleotide or a target gene in said plant or plant part.

In other aspects, a method of producing a transgenic plant or plant part having modulated expression of a target polynucleotide or target gene is provided, the method comprising: introducing into a plant or plant part a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector, thereby producing a transgenic plant or plant part having modulated expression of said target polynucleotide or target gene.

In further aspects, a method of producing a transgenic plant or plant part having modulated expression of a target polynucleotide or target gene is provided, the method comprising: introducing into said plant or plant part a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector; and regenerating a plant or plant part from said plant cell, thereby producing a transgenic plant or plant part having modulated expression of said target polynucleotide or target gene.

In additional aspects, recombinant nucleic acids, expression cassettes and/or vectors are provided, which can comprise a nucleotide sequence encoding a synthetic miRNA precursor of the invention.

The invention further provides plants, plant parts and cells comprising a synthetic miRNA precursor of the invention as well as seeds, crops, harvested products and post harvest products produced from the plants, plant parts, and/or crops of the invention.

These and other aspects of the invention are set forth in more detail in the description of the invention below.

BRIEF DESCRIPTION OF THE FIGURES

FIG. 1 shows a native miRNA precursors osa-MIR159 (rice) (SEQ ID NO:64), sbi-MIR159 (Sorghum) (SEQ ID NO:65), tae-MIR159 (wheat) (SEQ ID NO:66), and zma-MIR159 (maize)(SEQ ID NO:67).

FIG. 2 shows a chimeric zma-MIR159a-miR156 sequence (SEQ ID NO:68) in which miRNA precursor zma-pre-MIR159a is modified to replace the native miR159 guide sequence with a miR156 guide sequence

FIG. 4A shows wild type. FIG. 4B shows zma-MIR159-scrambled miR156 and FIG. 4C shows zma-MIR159a-miR156 and expressing miR156.

FIG. 5A shows a wild type maize plant. FIG. 5B shows a maize plant transformed with zma-MIR159a-miR156. FIG. 5C shows a plant transformed with a synthetic precursor of the invention (dp0019; SEQ ID NO:63) that expresses miR156 and FIG. 5D shows a plant transformed with zma-MIR159-scrambled miR156.

FIG. 10B is a blow-up of the section indicated in FIG. 10A between the red lines.

DETAILED DESCRIPTION OF THE INVENTION

Figure 3:
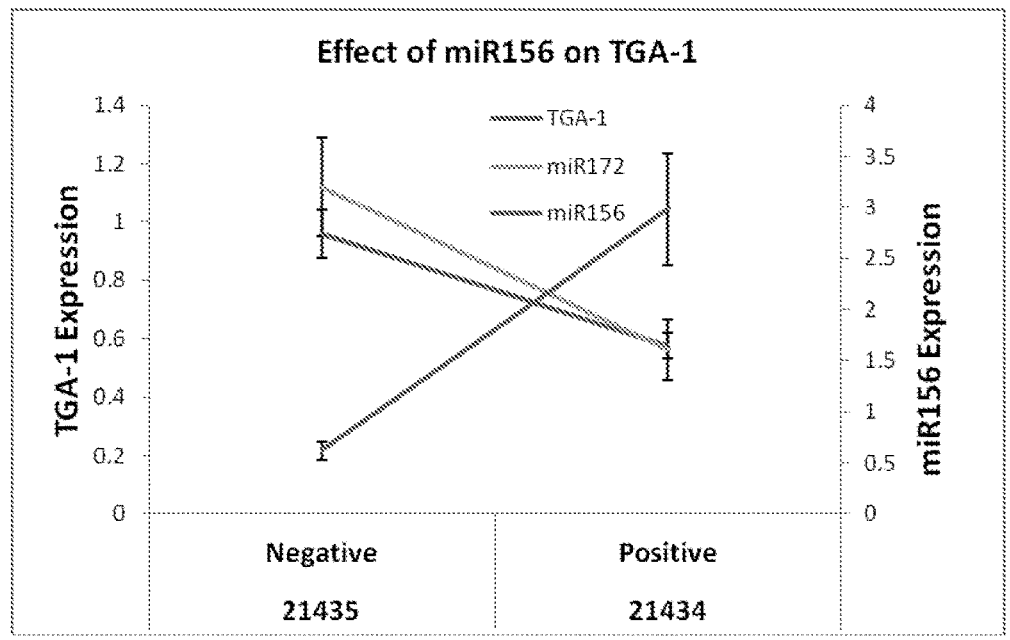
FIG. 3 shows the effect of expression of miR156 on TGA-1 and miR172 transcript levels.
Figure 4A:
FIG. 4A-4C show the grass-like phenotype resulting from expression of miR156 in maize.
Figure 4B:
Figure 4:
Figure 5A:
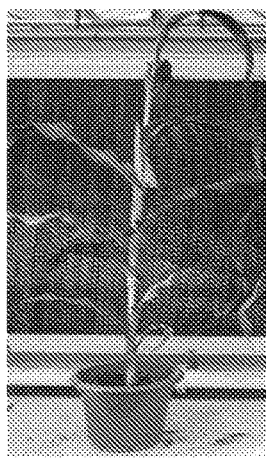
FIG. 5A-5D show the phenotype observed for wild type maize plants as compared to plants in which miR156 is overexpressed.
Figure 5B:
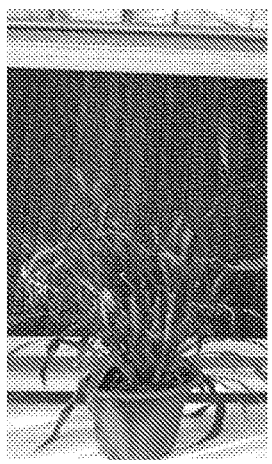
Figure 5C:
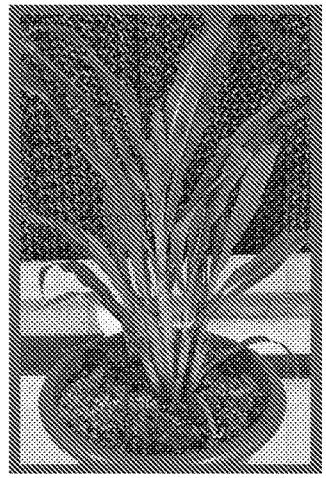
Figure 5D:
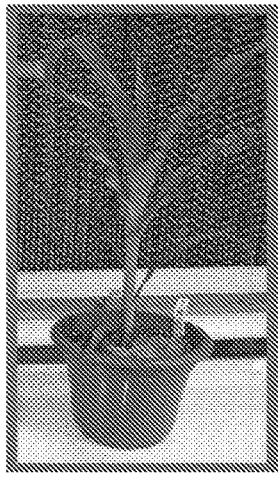

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications and patent applications mentioned in this specification are indicative of the level of skill of those skilled in the art that this invention pertains. Further, publications, patent applications, patents, and other references mentioned herein are incorporated by reference in their entireties for the teachings relevant to the sentence and/or paragraph in which the reference is presented.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, refers to variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof As used herein, the transitional phrase "consisting essentially of (and grammatical variants) means that the scope of a claim is to be interpreted to encompass the specified materials or steps recited in the claim and those that do not materially alter the basic and novel characteristic(s)" of the claimed invention. Thus, the term "consisting essentially of" when used in a claim of this invention is not intended to be interpreted to be equivalent to "comprising."

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

As used herein, the term "double strand" can mean 100% complementarity or less than 100% complementarity between the two strands of the double strand (e.g., about 60%, 65%, 70%, 75%, 80%, 85%, 90%, 95%, 99%, 100% complementarity, or any range or value therein).

As used herein, with respect to nucleic acids, the term "exogenous" refers to a nucleic acid molecule that is not in the natural genetic background of the cell/organism in which it resides. In some embodiments, the exogenous nucleic acid molecule comprises one or more nucleotide sequences that are not found in the natural genetic background of the cell/organism. In some embodiments, the exogenous nucleic acid molecule can comprise one or more additional copies of a nucleotide sequence that is/are endogenous to the cell/organism.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

As used herein, the term "heterologous" refers to a nucleotide/polypeptide that originates from a foreign species, or, if from the same species, is substantially modified from its native form in composition and/or genomic locus by deliberate human intervention.

The terms "increase," "increasing," "increased," "enhance," "enhanced," "enhancing," and "enhancement" (and grammatical variations thereof), as used herein, describe an elevation, for example, an elevation in the expression of a target gene or target polynucleotide (e.g., an elevation of at least about 20%, 25%, 30%, 35%, 40%, 45%, 50%, 75%, 100%, 125%, 150%, 175%, 200%, 350%, 300%, 350%, 400%, 450%, 500% or more). This increase in expression can be observed by, for example, comparing the expression of the target gene or target polynucleotide in a plant transformed with a synthetic precursor molecule of the invention comprising a guide miRNA complementary to the target gene or target polynucleotide to expression of said target gene or target polynucleotide in a control plant that, for example, is not transformed with said synthetic precursor molecule of the invention comprising a guide miRNA complementary to the same target gene or target polynucleotide.

As used herein, the terms "reduce," "reduced," "reducing," "reduction," "diminish," "suppress," and "decrease" (and grammatical variations thereof), describe, for example, a decrease in the expression of a target gene or target polynucleotide as compared to a control as described herein. This decrease in expression can be observed by comparing the expression of the target gene or target polynucleotide in a plant transformed with a synthetic precursor molecule of the invention comprising a guide miRNA complementary to the target gene or target polynucleotide to the expression of said target gene or target polynucleotide in a control plant that, for example, is not transformed with said synthetic precursor molecule of the invention comprising a guide miRNA complementary to the same target gene or target polynucleotide.

As used herein, the terms "modulating," "modulate," "modulates" or grammatical variations thereof, means an alteration in the expression of a target gene or target polynucleotide by increasing or reducing the expression of said target polynucleotide or target gene.

In some embodiments, the recombinant nucleic acid molecules, and/or nucleotide sequences of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature (i.e., non-naturally occurring). An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded functional nucleic acids or polypeptides are "isolated" in that, by the hand of man, they exist apart from their native environment and therefore are not products of nature, however, in some embodiments, they can be introduced into and exist in a recombinant host cell.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. As used herein, the term "substantially complementary" (and similar terms) means that two nucleic acid sequences are at least about 70%, 75%, 80%, 85%, 90%, 95%, 96%, 97%, 98%, 99% or more complementary. Alternatively, the term "substantially complementary" (and similar terms) can mean that two nucleic acid sequences can hybridize together under high stringency conditions (as described herein). Thus, in some embodiments, "substantially complementary" means about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% complementary, or any value or range therein).

The phrase "hybridizing specifically to" (and similar terms) refers to the binding, duplexing, or hybridizing of a molecule to a particular nucleic acid target sequence under stringent conditions when that sequence is present in a complex mixture (e.g., total cellular DNA or RNA) to the substantial exclusion of non-target nucleic acids, or even with no detectable binding, duplexing or hybridizing to non-target sequences. Selectively hybridizing sequences typically are at least about 40% complementary and are optionally substantially complementary or even completely complementary (i.e., 100% identical) to a target nucleic acid sequence.

The term "bind(s) substantially" (and similar terms) as used herein refers to complementary hybridization between a nucleic acid molecule and a target nucleic acid and embraces minor mismatches that can be accommodated by reducing the stringency of the hybridization media to achieve the desired detection of the target nucleic acid sequence.

The terms "gene silencing", "gene knockdown", "reduction of gene expression", "inhibition of gene expression", "gene downregulation", and "gene suppression" are used interchangeably to generally describe reductions of the amount of RNA transcribed from the gene and/or, in the case of a protein-encoding gene, protein translated from the transcribed mRNA. The transcribed RNA may be non-coding or protein-encoding. The term "non-coding" refers to polynucleotides that do not encode part or all of an expressed protein. Non-coding sequences include but are not limited to introns, enhancers, promoter regions, 3° untranslated regions, and 5' untranslated regions. Measurement of transcribed RNA or translated protein can be done by using molecular techniques such as RNA solution hybridization, nuclease protection, Northern hybridization, reverse transcription, gene expression monitoring with a microarray, antibody binding, enzyme-linked immunosorbent assay (ELISA), Western blotting, radioimmunoassay (RIA), other immunoassays, or fluorescence-activated cell analysis (FACS). Gene suppression can be the result of co-suppression, anti-sense suppression, transcriptional gene silencing, post-transcriptional gene silencing, or translational gene silencing. A "silenced", "knocked-down", "reduced", "inhibited", 'down regulated", or "suppressed" gene refers to a gene that is subject to silencing. "Target gene" is thus the gene which is to be silenced. Gene silencing is "specific" for a target gene when silencing of the target gene occurs without manifest effects on other genes.

In some embodiments, a miRNA can also result in increased expression of the target gene. Thus, in representative embodiments, a synthetic precursor of the invention (e.g., SEQ ID NO:9 and/or SEQ ID NOs:18-62).

"RNA interference" or "RNAi" refers to sequence-specific or gene-specific suppression of gene expression that is mediated by interfering RNA.

"Interfering RNA" is RNA capable of causing gene silencing. Interfering RNA encompasses any type of RNA molecule capable of down-regulating or silencing expression of a target gene, including but not limited to sense RNA, antisense RNA, short interfering RNA (siRNA), microRNA (miRNA), double-stranded RNA (dsRNA), hairpin RNA (RNA) and the like. Methods to assay for functional interfering RNA molecules are well-known in the art.

The phrases "target-specific small interfering RNAs," "target-specific siRNAs," "target-specific microRNAs," "target-specific miRNAs," "target-specific amiRNAs," and "target-specific nucleotide sequences" refer to interfering RNAs that have been designed to selectively or preferentially hybridize with nucleic acids in a target organism (the organism expressing or producing the miRNA).

Interfering RNA may be in the form of short double-stranded RNA (dsRNA) molecules like micro RNA (miRNA).

A dsRNA molecule need not be completely double-stranded, but comprises at least one double-stranded region comprising at least one functional double-stranded silencing element.

It is to be understood that the strands forming the at least one double-stranded region need not to be 100% complementary. Strands having insertions, deletions, and single point mutations relative to each other are still capable of forming a double-stranded region. Thus, the strands of the at least one double-stranded region of a dsRNA molecule are at least about 60%, 65%, 70%, 75%, 80%, 85%, 90%, 95%, 99%, or 100% complementary to each other.

It is also to be understood that the strands forming the at least one double-stranded silencing element (e.g., miRNA passenger strand/miRNA guide strand) need not be 100% complementary. Strands having insertions, deletions, and single point mutations relative to each other are still capable of forming a double-stranded silencing element. Thus, the strands of an at least one double-stranded silencing element of a dsRNA molecule can be at least about 80%, 85%, 90%, 95%, 99%, or 100% complementary to each other.

In representative embodiment, a guide strand (targeting strand) and a passenger strand of a synthetic miRNA precursor of the invention can be at least about 70% to about 90% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%), or about 80% to about 90% (e.g., about 80%, 81%, 82%, 83%, 84%, 85%, 86%, 87%, 88%, 89%, 90%) complementary to each other, or any value or range therein.

In some aspects, a dsRNA may be a single strand that is capable of folding back on itself to form a hairpin RNA (hpRNA) or stem-loop structure. In the case of a hpRNA, the double-stranded region or 'stem' is formed from two regions or segments of the RNA that are essentially inverted complements of one another and possess sufficient complementarity to allow the formation of a double-stranded region. At least one functional double-stranded silencing element is present in this double-stranded region or 'stem' of the molecule. The stem-forming single-stranded regions are typically separated by a region or segment of the RNA known as the 'loop' region. This region can comprise any nucleotide sequence conferring enough flexibility to allow self-pairing to occur between the flanking complementary regions of the RNA. In general, the loop region is substantially single-stranded and acts as a spacer element between the inverted complements. In some representative embodiments, further loops and double stranded regions can be comprised within a larger loop region.

As used herein, the term "mismatch" comprises one or more mismatched nucleotides, unless otherwise indicated by the context.

As used herein, the term "bulge" comprises one or more unopposed nucleotides.

"Target gene" refers to the entire target gene, including exons, introns and regulatory regions such as promoters, enhancers, and terminators, 5' and 3' untranslated regions, the primary transcript, and the mature mRNA. "Target gene sequence" refers to either the nucleotide sequence of the sense strand of the entire target gene, including exons, introns and regulatory sequences such as promoters, enhancers, and terminators, 5' and 3' untranslated regions, the nucleotide sequence of the primary transcript, and/or the nucleotide sequence of the mature mRNA. The sense strand of a gene is the strand that is (partially) copied during transcription.

A target gene may be a gene whose silencing has a high likelihood of resulting in a strong phenotype, preferably a knockout or null phenotype. Such target genes are often those whose protein products are involved in core cellular processes such as DNA replication, cell cycle, transcription, RNA processing, translation, protein trafficking, secretion, protein modification, protein stability and degradation, energy production, intermediary metabolism, cell structure, signal transduction, channels and transporters, and endocytosis. In a preferred embodiment, it is advantageous to select a gene for which a small decrease in expression levels results in deleterious or positive effects for the targeted organism.

A "target polynucleotide" refers to any nucleic acid that is of interest as a target for modulation of expression. A miRNA guide strand (or targeting strand) can be fully or substantially complementary (e.g., imperfect complementarity) to a target polynucleotide or to a portion or fragment of a target gene sequence.

"Target polynucleotide" thus, refers to the part of a target gene which is bound or hybridized by the targeting strand (guide strand) of the at least one double-stranded silencing element (e.g., guide/passenger strand) of the interfering RNA molecule (e.g., miRNA precursor molecule). The target polynucleotide may correspond to a fragment of the whole target gene. Therefore, the target polynucleotide may comprise at least about 17, 18, 19, 20, 21, 22, 23, 24, 25 contiguous nucleotides of the target gene. The targeting strand similarly may be at least about 17, 18, 19, 20, 21, 22, 23, 24, 25 nucleotides long. However, the target polynucleotide and the targeting strand need not be equal in length.

The skilled person is aware of methods for identifying the most suitable target polynucleotide within the context of the full-length target gene. For example, multiple double-stranded silencing elements targeting different target polynucleotides can be synthesized and tested. Alternatively, digestion of the RNA transcript with enzymes such as RNAse H can be used to determine sites of the RNA that are in a conformation susceptible to gene silencing. Target polynucleotides may also be identified using in silico approaches, for example, the use of computer algorithms designed to predict the efficacy of gene silencing based on targeting different regions within the full-length target gene.

As used herein, "operatively associated with," "operatively linked to," or "operably linked to," when referring to a first nucleic acid sequence that is operatively linked to a second nucleic acid sequence, means a situation when the first nucleic acid sequence is placed in a functional relationship with the second nucleic acid sequence. For instance, a promoter is operatively linked to a coding sequence if the promoter effects the transcription or expression of the coding sequence.

A DNA "promoter" is an untranslated DNA sequence upstream of a coding region that contains the binding site for RNA polymerase and initiates transcription of the DNA. A "promoter region" can also include other elements that act as regulators of gene expression. Promoters can include, for example, constitutive, inducible, temporally regulated, developmentally regulated, chemically regulated, tissue-preferred and tissue-specific promoters for use in the preparation of recombinant nucleic acid molecules, i.e., chimeric genes. In particular aspects, a "promoter" useful with the invention is a promoter capable of initiating transcription of a nucleotide sequence in a cell of a plant.

A "chimeric gene" is a recombinant nucleic acid molecule in which a promoter or other regulatory nucleotide sequence is operatively associated with a nucleotide sequence that codes for an mRNA or which is expressed as a protein, such that the regulatory nucleotide sequence is able to regulate transcription or expression of the associated nucleotide sequence. The regulatory nucleotide sequence of the chimeric gene is not normally operatively linked to the associated nucleotide sequence as found in nature.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

"Identity" or "percent identity" refers to the degree of similarity between two nucleic acid or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

In some embodiments, two nucleotide sequences can also be considered to be substantially complementary when the two sequences hybridize to each other under stringent conditions. In some representative embodiments, two nucleotide sequences considered to be substantially complementary hybridize to each other under highly stringent conditions.

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences. Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions.

For DNA-DNA hybrids, the T. can be approximated from the equation of Meinkoth and Wahl, Anal. Biochem., 138: 267-84 (1984): $T_m=81.5°$ C.+16.6 (log M)+0.41 (% GC)-0.61 (% formamide)-500/L; where M is the molarity of monovalent cations, % GC is the percentage of guanosine and cytosine nucleotides in the DNA, % formamide is the percentage of formamide in the hybridization solution, and L is the length of the hybrid in base pairs. The T. is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired degree of identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, highly stringent conditions can utilize a hybridization and/or wash at the thermal melting point ($T_m$) or 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). If the desired degree of mismatching results in a T. of less than 45° C. (aqueous solution) or 32° C. (formamide solution), optionally the SSC concentration can be increased so that a higher temperature can be used. An extensive guide to the hybridization of nucleic acids is found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier, New York (1993); Current Protocols in Molecular Biology, chapter 2, Ausubel, et al., eds, Greene Publishing and Wiley-Interscience, New York (1995); and Green & Sambrook, In: Molecular Cloning, A Laboratory Manual, 4th Edition, Cold Spring Harbor Press, Cold Spring Harbor, N.Y. (2012).

Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M $NaPO_4$, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

Nucleic acids that do not hybridize to each other under stringent conditions are still substantially identical if the proteins that they encode are substantially identical (e.g., due to the degeneracy of the genetic code).

A nucleic acid sequence is "isocoding with" a reference nucleic acid sequence when the nucleic acid sequence encodes a polypeptide having the same amino acid sequence as the polypeptide encoded by the reference nucleic acid sequence.

As used herein, the terms "transformation," "transfection," and "transduction" refer to the introduction of an exogenous/heterologous nucleic acid (RNA and/or DNA) into a host cell. A cell has been "transformed," "transfected" or "transduced" with an exogenous/heterologous nucleic acid when such nucleic acid has been introduced or delivered into the cell.

As used herein with respect to plants and plant parts, the term "transgenic" refers to a plant, plant part or plant cell that comprises one or more exogenous nucleic acids. Generally, the exogenous nucleic acid is stably integrated within the genome such that the polynucleotide is passed on to successive generations. The exogenous nucleic acid may be integrated into the genome alone or as part of a recombinant expression cassette. "Transgenic" may be used to designate any plant, plant part or plant cell the genotype of which has been altered by the presence of an exogenous nucleic acid, including those transgenics initially so altered and those created by sexual crosses or asexual propagation from the initial transgenic. As used herein, the term "transgenic" does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The invention is directed in part to the development of synthetic miRNA precursor molecules for the delivery to plants of miRNAs that target specific nucleic acids (e.g., gene or nucleic acid targets) for modulating the expression of said targets in the plant.

Accordingly, in some aspects of the invention, a synthetic miRNA precursor (nucleic acid) molecule is provided, comprising, consisting essentially of or consisting of the following structure 5' to 3':

A-B-C-D-E-F, wherein

A is a nucleotide sequence that is optionally present and when present comprises a first strand (A') and a second strand (A") each of which independently comprise 1 to 22 nucleotides;

B is a nucleotide sequence comprising a first strand (B') and a second strand (B"), wherein the first strand comprises a miRNA passenger strand having a nucleotide sequence of $GNGN_{15-22}$ (SEQ ID NO:1) and the second strand comprises a miRNA guide strand having the nucleotide sequence of $UN_{16-23}C$ (SEQ ID NO:2) and the passenger strand and the guide strand form a double stranded sequence having three mismatches. In some embodiments, each of the three mismatches may comprise a length of one base pair. In some embodiments, two of the three mismatches may comprise a length of one base pair, while the remaining mismatch may comprise a length of two to three contiguous nucleotides, wherein mismatch comprising a length of two to three contiguous nucleotides can be at the 5' end (toward base) or the 3' end of B (toward loop).

C is a nucleotide sequence comprising a first strand (C') and a second strand (C"), wherein the first strand comprises a nucleotide sequence of GA[A/G][G/C]GGGCC-UACGGACGGUGUUGU (SEQ ID NO:3), and the second strand comprises a nucleotide sequence of ACCACACC-GUCCGGGCCC[G/C][C/A]UC (SEQ ID NO:4), and the first strand and second strand form a double stranded sequence comprising two to four mismatches or bulges, or any combination thereof;

D is a nucleotide sequence comprising a first strand (D') and a second strand (D"), wherein the first strand comprises a nucleotide sequence of UCCGCUGC[U/C]CGUUCAUG (SEQ ID NO:5), and the second strand comprises a nucleotide sequence of CAUGACCG[A/G]GGAGCUGC (SEQ ID NO:6) and the first strand and second strand form a double stranded sequence comprising two to four mismatches;

E is a nucleotide sequence comprising a first strand (E') and a second strand (E"), wherein the first strand comprises a nucleotide sequence of GUUCCC[C/A][A/C]UAUCUA-CUUCCA (SEQ ID NO:7), and the second strand comprises a nucleotide sequence of UGGAAGUAGCUU[U/G][G/U] GGUUUG (SEQ ID NO:8) and the first strand and second strand form a double stranded sequence comprising two mismatches; and F is a sequence comprising a length of 10 to 50 nucleotides and forming a loop. In some aspects the invention provides a synthetic miRNA precursor comprising the nucleotide sequence of SEQ ID NO:9.

It is to be understood that, from 5' to 3', the first strand of A (A') (when A is present) is contiguous with the first strand of B (B'), which is contiguous with the first strand of C (C'), which is contiguous with the first strand of D (D'), which is contiguous with the first strand of E (E'), which is contiguous with F, which is contiguous with the second strand of E (E"), which is contiguous with the second strand of D (D"), which is contiguous with the second strand of C (C"), which is contiguous with the second strand of B (B"), which is contiguous with the second strand of A (A") (when A is present).

In some aspects, the three mismatches of B of a synthetic miRNA precursor molecule of the invention comprise, consist essentially of, or consist of: a first mismatch formed between the 5' nucleotide U of SEQ ID NO:2 and the 3' most nucleotide of SEQ ID NO:1, a second single nucleotide mismatch formed six nucleotides (including the mismatched nucleotide) upstream (5') of the first mismatch and a third single nucleotide mismatch formed four nucleotides (including the mismatched nucleotide) upstream (5') of the second mismatch. When one of the three mismatches of B comprises a length of 2-3 contiguous nucleotides, the relative positions of the three mismatches will be adjusted accordingly.

In some aspects, the mismatches and/or bulges of C of a synthetic miRNA precursor molecule of the invention comprise, consist essentially of, or consist of a length of one to three nucleotides.

In other aspects, the mismatches of D of a synthetic miRNA precursor molecule of the invention comprise, consist essentially of, or consist of a length of one to three nucleotides.

In additional aspects, C of a synthetic miRNA precursor molecule of the invention comprises, consists essentially of, or consists of one single nucleotide mismatch, one two nucleotide mismatch, and one bulge having two unopposed nucleotides.

In some aspects, the 5' nucleotides of SEQ ID NO:3 (C'), GA, bind to the 3' nucleotides of SEQ ID NO:4 (C"), UC, to form a double strand.

In some aspects, a (third) DCL-1 cleavage site is formed in a synthetic miRNA precursor molecule of the invention at the 3' end region of B and the 5' end region of C by the binding of the 5' nucleotides of SEQ ID NO:3 (C'), GA, to the 3' nucleotides of SEQ ID NO:4 (C"), UC, and a mismatch formed between the 5' nucleotide of SEQ ID NO:2 (B"), U, and the 3' most nucleotide of SEQ ID NO:1 (B'). As used herein, "3' end region" and "5' end region" refers to the region near or comprising the 3' end of a sequence or the region near or comprising the 5' end of a sequence and does not refer specifically to the junction of the 3' end of a sequence (e.g., B) and the 5' end of the next contiguous sequence (e.g., C). As used herein, "near" the 5' or 3' end means within about one to five nucleotides of the 5' or 3' end of the nucleotide sequence (e.g., about 1, 2, 3, 4, 5 nucleotides).

In other aspects, D of a synthetic miRNA precursor molecule of the invention comprises, consists essentially of, or consists of three mismatches. In some aspects, D of a synthetic miRNA precursor molecule of the invention comprises, consists essentially of, or consists of two single nucleotide mismatches and one three nucleotide mismatch. In some aspects, the 5' nucleotides UCC of SEQ ID NO:5 (D'), form a mismatch with the 3' nucleotides UG[C/A] of SEQ ID NO:6 (D").

In additional aspects, the 3' nucleotides GU of SEQ ID NO:3 (C'), bind to the 5' nucleotides AC of SEQ ID NO:4 (C"), to form a double strand. In some aspects, a (second) DCL-1 cleavage site is formed in a synthetic miRNA precursor molecule of the invention at the 3' end of C and the 5' end of D by the binding of the 3' nucleotides GU of SEQ ID NO:3 (C'), to the 5' nucleotides AC of SEQ ID NO: 4 (C'), and the mismatch formed between the 5' nucleotides UCC of SEQ ID NO: 5 (D'), and the 3' nucleotides UG[C/A] of SEQ ID NO: 6 (D").

In some aspects, the mismatches of E of a synthetic miRNA precursor molecule of the invention comprise, consist essentially of, or consist of a length of three to four nucleotides. In other aspects, E of a synthetic miRNA precursor molecule of the invention comprises, consists essentially of, or consists of two mismatches, a four nucleotide mismatch, and a three nucleotide mismatch. In some aspects, a four nucleotide mismatch is formed between the 5' nucleotides GUUC of SEQ ID NO:7 (E'), and the 3' nucleotides UUUG of SEQ ID NO:8 (E"), and a three nucleotide mismatch is formed between the nucleotides UAU of SEQ ID NO: 7 (E'), and the nucleotides CUU of SEQ ID NO:8 (E"). In some aspects, between the two mismatches of E in a synthetic miRNA precursor molecule of the invention, a double strand is formed comprising, consisting essentially of or consisting of nucleotides CC[C/A][A/C] of SEQ ID NO:7 (E') and nucleotides [U/G][G/U]GG of SEQ ID NO:8 (E"). In some aspects of the invention, a (first) DCL-1 cleavage site is formed in E by the four nucleotide mismatch formed between the 5' nucleotides GUUC of SEQ ID NO:7 (E'), and the 3' nucleotides UUUG of SEQ ID NO:8 (E"), and the double strand formed between nucleotides CC[C/A][A/C] of SEQ ID NO:7 (E') and nucleotides [U/G][G/U]GG of SEQ ID NO:8 (E").

In some aspects of the invention, F comprises, consists essentially of, or consists of a nucleotide sequence having a length of 14 to 44 nucleotides, optionally a length of 14 to 21 nucleotides. In other aspects, F comprises, consists essentially of, or consists of a nucleotide sequence of UCAUGUUAUAGAUCUCGUCUU (SEQ ID NO:10), UCAUGUUAUAGAUCUCGU (SEQ ID NO:11), UGUUAUAGAUCUCG (SEQ ID NO:12), UCAGAGAGAGAGAGAGAUGUC (SEQ ID NO:13), UCAUGUGUAUAUAUGUAAUCCAUGGGGAGG-GUUCUCUCGUCUU (SEQ ID NO:14), or UCAUC-UUAUACAUCUCCU (SEQ ID NO:15).

In some aspects, the synthetic miRNA precursor molecule can be about 150 to about 300 or more nucleotides in length.

In some aspects, the invention provides a synthetic miRNA precursor comprising, consisting essentially of or consisting of the nucleotide sequence of SEQ ID NO:9.

In some aspects, the invention provides a synthetic miRNA precursor comprising, consisting essentially of or consisting of any one of the polynucleotide sequences listed in Table 1 (SEQ ID NO:9 and/or SEQ ID NOs:18-62). In some aspects, the invention provides a synthetic miRNA precursor comprising, consisting essentially of or consisting of a nucleotide sequence that is substantially identical (e.g., at least about 70% to about 99% identical) or that has at least about 90% identity (e.g., 90%, 91%, 92%, 93%, 94%, 95%, 96%, 97%, 98%, 99% or more identity) to any one of the polynucleotide sequences listed in Table 1 (SEQ ID NO:9 and/or SEQ ID NOs:18-62). In some aspects, the invention provides a synthetic miRNA precursor comprising, consisting essentially of or consisting of a nucleotide sequence that is substantially identical or that has at least about 90% identity to any one of the polynucleotide sequences listed in Table 1 (SEQ ID NO:9 and/or SEQ ID NOs:18-62) when B (i.e., guide and passenger strand) is not included in the calculation of percent identity. In some aspects, the invention provides a synthetic miRNA precursor comprising, consisting essentially of or consisting of a nucleotide sequence that is substantially identical or that has at least about 90% identity to any one of the polynucleotide sequences listed in Table 1 (SEQ ID NO:9 and/or SEQ ID NOs:18-62) when B (i.e., guide and passenger strand) and F (loop) are not included in the calculation of percent identity. In some aspects, the invention provides a synthetic miRNA precursor comprising, consisting essentially of or consisting of a nucleotide sequence that is substantially identical or that has at least about 90% identity to any one of the polynucleotide sequences listed in Table 1 (SEQ ID NO:9 and/or SEQ ID NOs:18-62) when B (i.e., guide and passenger strand), F (loop), and A, when present, are not included in the calculation of percent identity.

TABLE 1

| miRNA Precursor Sequence (5'→3') | SEQ ID NO: |
|---|---|
| $N_{0-50}$GNGN$_{15-22}$GARSGGGCCUACGGACGGUGUU-GUUCCGCUG CYCGUUCAUGGUUCCCMMUAUCUACUUCCA($N_{10-50}$) UGGAA GUAGCUUKKGGUUUGCAUGACCGRGGAGCUGCACCACACC GUCCGGGCCCSMUCUN$_{16-23}$CN$_{0-50}$ | 9 |
| GNGN$_{15-22}$GARSGGGCCUACGGACGGUGUUGUUCCGCUGCYC GUUCAUGGUUCCCMMUAUCUACUUCCA($N_{10-50}$) UGGAAGGU AGCUUKKGGUUUGCAUGACCGRGGAGCUGCACCACACCGUC CGGGCCCSMUCUN$_{16-23}$C | 18 |
| GNGN$_{15-22}$GARSGGGCCUACGGACGGUGUUGUUCCGCUGCYC GUUCAUGGUUCCCMMUAUCUACUUCCA($N_{14-50}$) UGGAAGUA GCUUKKGGUUUGCAUGACCGRGGAGCUGCACCACACCGUCC GGGCCCSMUCUN$_{16-23}$C | 19 |
| GNGN$_{15-22}$GARSGGGCCUACGGACGGUGUUGUUCCGCUGCYC GUUCAUGGUUCCCMMUAUCUACUUCCA($N_{10-44}$) UGGAAGUA GCUUKKGGUUUGCAUGACCGRGGAGCUGCACCACACCGUCC GGGCCCSMUCUN$_{16-23}$C | 20 |
| GNGN$_{15-22}$GARSGGGCCUACGGACGGUGUUGUUCCGCUGCYC GUUCAUGGUUCCCMMUAUCUACUUCCA($N_{10-21}$) UGGAAGUA GCUUKKGGUUUGCAUGACCGRGGAGCUGCACCACACCGUCC GGGCCCSMUCUN$_{16-23}$C | 21 |
| GNGN$_{15-22}$GARSGGGCCUACGGACGGUGUUGUUCCGCUGCYC GUUCAUGGUUCCCMMUAUCUACUUCCAUCAUGUUAUAGAUC UCGUCUUUGGAAGUAGCUUKKGGUUUGCAUGACCGRGGAGC UGCACCACACCGUCCGGGCCCSMUCUN$_{16-23}$C | 22 |
| GNGN$_{15-22}$GARSGGGCCUACGGACGGUGUUGUUCCGCUGCYC GUUCAUGGUUCCCMMUAUCUACUUCCAUCAUGUUAUAGAUC UCGUUGGAAGUAGCUUKKGGUUUGCAUGACCGRGGAGCUGC ACCACACCGUCCGGGCCCSMUCUN$_{16-23}$C | 23 |

TABLE 1-continued

| miRNA Precursor Sequence (5'→3') | SEQ ID NO: |
|---|---|
| GNGN$_{15-22}$GARSGGGCCUACGGACGGUGUUGUUCCGCUGCYCGUUCAUGGUUCCCMMUAUCUACUUCC<u>AUGUUAUAGAUCUCG</u>UGGAAGUAGCUUKKGGUUUGCAUGACCGRGGAGCUGCACCACACCGUCCGGGCCCSMUCUN$_{16-23}$C | 24 |
| GNGN$_{15-22}$GARSGGGCCUACGGACGGUGUUGUUCCGCUGCYCGUUCAUGGUUCCCMMUAUCUACUUCC<u>AUCAGAGAGAGAGAGAGAUG</u>UGGAAGUAGCUUKKGGUUUGCAUGACCGRGGAGCUGCACCACACCGUCCGGGCCCSMUCUN$_{16-23}$C | 25 |
| GNGN$_{15-22}$GARSGGGCCUACGGACGGUGUUGUUCCGCUGCYCGUUCAUGGUUCCCMMUAUCUACUUCC<u>AUCAUGUGUAUAUAUGUAAUCCAUGGGGGAGGGUUCUCUCGUCUUUGGAAGUAGCU</u>UKKGGUUUGCAUGACCGRGGAGCUGCACCACACCGUCCGGGCCCSMUCUN$_{16-23}$C | 26 |
| GNGN$_{15-22}$GARSGGGCCUACGGACGGUGUUGUUCCGCUGCYCGUUCAUGGUUCCCMMUAUCUACUUCC<u>AUCAUCUUAUAUCAUCUCC</u>UUGGAAGUAGCUUKKGGUUUGCAUGACCGRGGAGCUGCACCACACCGUCCGGGCCCSMUCUN$_{16-23}$C | 27 |
| N$_{1-22}$GNGN$_{15-22}$GARSGGGCCUACGGACGGUGUUGUUCCGCUGCYCGUUCAUGGUUCCCMMUAUCUACUUCCA(N$_{10-50}$)UGGAAGUAGCUUKKGGUUUGCAUGACCGRGGAGCUGCACCACACCGUCCGGGCCCSMUCUN$_{16-23}$CN$_{1-22}$ | 28 |
| N$_{1-22}$GNGN$_{15-22}$GARSGGGCCUACGGACGGUGUUGUUCCGCUG CYCGUUCAUGGUUCCCMMUAUCUACUUCCA(N$_{14-44}$) UGGAAGUAGCUUKKGGUUUGCAUGACCGRGGAGCUGCACCACACCGUCC GGGCCCSMUCUN$_{16-23}$CN$_{1-22}$ | 29 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCCA(N$_{10-50}$) UGGAAGUAGCUUKKGGUUUGCAUGACCGRGGAGCUGCACCACACCGUCCGGGCCCSMUCUN$_{16-23}$*CAUCCUAA CACCUGCCAUUGU* | 30 |
| *UUUGAA*GNGN$_{15-22}$GARSGGGCCUACGGACGGUGUUGUUCCGCUGCYCGUUCAUGGUUCCCMMUAUCUACUUCCA(N$_{10-50}$) UGGAAGUAGCUUKKGGUUUGCAUGACCGRGGAGCUGCACCACACCGUCC GGGCCCSMUCUN$_{16-23}$*CAUCCUA* | 31 |
| *GRUUUGAA*GNGN$_{15-22}$GARSGGGCCUACGGACGGUGUUGUUCCGCUGCYCGUUCAUGGUUCCCMMUAUCUACUUCCA(N$_{10-50}$)U GGAAGUAGCUUKKGGUUUGCAUGACCGRGGAGCUGCACCACACCGUCCGGGCCCSMUCUN$_{16-23}$*CWAGUCCUA* | 32 |
| *GA*GNGN$_{15-22}$GARSGGGCCUACGGACGGUGUUGUUCC GCUGCYCGUUCAUGGUUCCCMMUAUCUACUUCCA(N$_{10-50}$) UGGAAGUAGCUUKKGGUUUGCAUGACCGRGGAGCUGCACCACACCGUCCGGGCCCSMUCUN$_{16-23}$*CUCUA* | 33 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCCA(N$_{14-44}$) UGGAAGUAGCUUKKGGUUUGCAUGACCGRGGAGCUGCACCACACCGUCCGGGCCCSMUCUN$_{16-23}$*CAUCCUAA CACCUGCCAUUGU* | 34 |
| *UUUGAA*GNGN$_{15-22}$GARSGGGCCUACGGACGGUGUUGUUCCGCUGCYCGUUCAUGGUUCCCMMUAUCUACUUCCA(N$_{14-44}$) UGGAAGUAGCUUKKGGUUUGCAUGACCGRGGAGCUGCACCACACCGUCCGGGCCCSMUCUN$_{16-23}$*CAUCCUA* | 35 |
| *GRUUUGAA*GNGN$_{15-22}$GARSGGGCCUACGGACGGUGUUGUUCGCUGCYCGUUCAUGGUUCCCMMUAUCUACUUCCA(N$_{14-44}$)U GGAAGUAGCUUKKGGUUUGCAUGACCGRGGAGCUGCACCACACCGUCCGGGCCCSMUCUN$_{16-23}$*CWA GUCCUA* | 36 |
| *GA*GNGN$_{15-22}$GARSGGGCCUACGGACGGUGUUGUUCCGCUGCYCGUUCAUGGUUCCCMMUAUCUACUUCCA(N$_{14-44}$) UGGAAGUAGCUUKKGGUUUGCAUGACCGRGGAGCUGCACCACACCGUCCGGGCCCSMUCUN$_{16-23}$*CUCUA* | 37 |
| *GCGUUAUUCGGUGUUUGAA*GNGN$_{15-22}$GARSGGGCCUACGGACGGUGUUGUUCCGCUGCYCGUUCAUGGUUCCCMMUAGCUUKKGGUUUGCAUGACCGRGGAGCUGCACCACACCGUCCGGGCCCSMUCUN$_{16-23}$*CAUCCUAACACCUGCCAUUGU* | 38 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCC<u>AUCAUGUUAUAGAUCUCG</u>UGGAAGUAGCUUKKGGUUUGCAUGACCGRGGAGCUGCACCACACCGUCCGGGCCCSMUCUN$_{16-23}$*CAUCCUAACACCUGCCAUUGU* | 39 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCC<u>AUGUUAUAGAUCUCG</u>UGGAAGUAGCUUKKGGUUUGCAUGACCGRGGAGCUGCACCACACCGUCCGGGCCCSMUCUN$_{16-23}$*CAUCCUAACACCUGCCAUUGU* | 40 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCC<u>AUCAGAGAGAGAGAGAGAUGCU</u>GGAAGUAGCUUKKGGUUUGCAUGACCGRGGAGCUGCACCACACCGUCCGGGCCCSMUCUN$_{16-23}$*CAUCCUAACACCUGCCAUUGU* | 41 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCC<u>AUCAUGUGUAUAUAUGUAAUCCAUGGGGGAGGGUUCUCUCGUCUUUGGAAGUAGCU</u>UKKGGUUUGCAUGACCGRGGAGCUGCACCACACCGUCCGGGCCCSMUCUN$_{16-23}$*CAUCCUAACACCUGCCAUUGU* | 42 |
| *GCGUUAUUCGGUGUUUGAA*GNGN$_{15-22}$GARSGGGCCUACGGACGGUGUUGUUCCGCUGCYCGUUCAUGGUUCCCMMUAUCUACUUCC<u>AUCUUAUAUACAUCUCC</u>UUGGAAGUAGCUUKKGGUUUGCAUGACCGRGGAGCUGCACCACACCGUCCGGGCCCSMUCUN$_{16-23}$*CAUCCUAACACCUGCCAUUGU* | 43 |
| *UUUGAA*GNGN$_{15-22}$GARSGGGCCUACGGACGGUGUUGUUCCGCUGCYCGUUCAUGGUUCCCMMUAUCUACUUCC<u>AUCAUGUUAUAGAUCUCGUCUUUGGAAGUAGCU</u>UKKGGUUUGCAUGACCGRGGAGCUGCACCACACCGUCCGGGCCCSMUCUN$_{16-23}$*CAUCCUA* | 44 |
| *UUUGAA*GNGN$_{15-22}$GARSGGGCCUACGGACGGUGUUGUUCCGCUGCYCGUUCAUGGUUCCCMMUAUCUACUUCC<u>AUCAUGUUAUAGAUCUCG</u>UGGAAGUAGCUUKKGGUUUGCAUGACCGRGGAGCUGCACCACACCGUCCGGGCCCSMUCUN$_{16-23}$*CAUCCUA* | 45 |
| *UUUGAA*GNGN$_{15-22}$GARSGGGCCUACGGACGGUGUUGUUCCGCUGCYCGUUCAUGGUUCCCMMUAUCUACUUCC<u>AUGUUAUAGAUCUCG</u>UGGAAGUAGCUUKKGGUUUGCAUGACCGRGGAGCUGCACCACACCGUCCGGGCCCSMUCUN$_{16-23}$*CCAUCCUA* | 46 |
| *UUUGAA*GNGN$_{15-22}$GARSGGGCCUACGGACGGUGUUGUUCCGCUGCYCGUUCAUGGUUCCCMMUAUCUACUUCC<u>AUCAGAGAGAGAGAGAGAUGCU</u>GGAAGUAGCUUKKGGUUUGCAUGACCGRGGAGCUGCACCACACCGUCCGGGCCCSMUCUN$_{16-23}$*CAUCCUA* | 47 |
| *UUUGAA*GNGN$_{15-22}$GARSGGGCCUACGGACGGUGUUGUUCCGCUGCYCGUUCAUGGUUCCCMMUAUCUACUUCC<u>AUCAUGUGUAUAUAUGUAAUCCAUGGGGGAGGGUUCUCUCGUCUUUGGAAGUAGCU</u>UKKGGUUUGCAUGACCGRGGAGCUGCACCACACCGUCCGGGCCCSMUCUN$_{16-23}$*CAUCCUA* | 48 |
| *UUUGAA*GNGN$_{15-22}$GARSGGGCCUACGGACGGUGUUGUUCCGCUGCYCGUUCAUGGUUCCCMMUAUCUACUUCC<u>AUCAUCUUAUACAUCUCCUUGGAAGUAGCU</u>UKKGGUUUGCAUGACCGRGGAGCUGCACCACACCGUCCGGGCCCSMUCUN$_{16-23}$*CAUCCUA* | 49 |
| *GRUUUGAA*GNGN$_{15-22}$GARSGGGCCUACGGACGGUGUUGUUCGCUGCYCGUUCAUGGUUCCCMMUAUCUACUUCC<u>AUCAUGUUAUAGAUCUCGUCUUUGGAAGUAGCU</u>UKKGGUUUGCAUGACCGRGGAGCUGCACCACACCGUCCGGGCCCSMUCUN$_{16-23}$*CCWAGUCCUA* | 50 |
| *GRUUUGAA*GNGN$_{15-22}$GARSGGGCCUACGGACGGUGUUGUUCGCUGCYCGUUCAUGGUUCCCMMUAUCUACUUCC<u>AUCAUGUUAUAGAUCUCG</u>UGGAAGUAGCUUKKGGUUUGCAUGACCGRGGAGCUGCACCACACCGUCCGGGCCCSMUCUN$_{16-23}$*CCWAGUCCUA* | 51 |

TABLE 1-continued

| miRNA Precursor Sequence (5'→3') | SEQ ID NO: |
|---|---|
| GRUUUGAAGNGN$_{15-22}$GARSGGGCCUACGGACGGUGUUGUUC CGCUGCYCGUUCAUGGUUCCCMMUAUCUACUUCC<u>AUGUUAU AGAUCUCG</u>UGGAAGUAGCUUKKGGUUUGCAUGACCGRGGAG CUGCACCACACCGUCCGGGCCCSMUCUN$_{16-23}$CCWAGUCC UA | 52 |
| GRUUUGAAGNGN$_{15-22}$GARSGGGCCUACGGACGGUGUUGUUC CGCUGCYCGUUCAUGGUUCCCMMUAUCUACUUCC<u>AUCAGAG AGAGAGAGAGAUGUC</u>UGGAAGUAGCUUKKGGUUUGCAUGAC CGRGGAGCUGCACCACACCGUCCGGGCCCSMUCUN$_{16-23}$CC WAGUCCUA | 53 |
| GRUUUGAAGNGN$_{15-22}$GARSGGGCCUACGGACGGUGUUGUUC CGCUGCYCGUUCAUGGUUCCCMMUAUCUACUUCC<u>AUCAUGU GUAUAUAUGUAAUCCAUGGGGGAGGG</u>UUCUCUCGUCUUUUG GAAGUAGCUUKKGGUUUGCAUGACCGRGGAGCUGCACCACA CCGUCCGGGCCCSMUCUN$_{16-23}$CCWAGU CCUA | 54 |
| GRUUUGAAGNGN$_{15-22}$GARSGGGCCUACGGACGGUGUUGUUC CGCUGCYCGUUCAUGGUUCCCMMUAUCUACUUCC<u>AUCAUCU UAUACAUCUCC</u>UUGGAAGUAGCUUKKGGUUUGCAUGACCGR GGAGCUGCACCACACCGUCCGGGCCCSMUCUN$_{16-23}$CCWAG UCCUA | 55 |
| GAGNGN$_{15-22}$GARSGGGCCUACGGACGGUGUUGUUCCGCUGC YCGUUCAUGGUUCCCMMUAUCUACUUCC<u>AUCAUGUUAUAGA UCUCGUCUUUUG</u>GAAGUAGCUUKKGGUUUGCAUGACCGRGGA GCUGCACCACACCGUCCGGGCCCSMUCUN$_{16-23}$CUCUA | 56 |
| GAGNGN$_{15-22}$GARSGGGCCUACGGACGGUGUUGUUCCGCUGC YCGUUCAUGGUUCCCMMUAUCUACUUCC<u>AUCAUGUUAUAGA UCUCG</u>UGGAAGUAGCUUKKGGUUUGCAUGACCGRGGAGCU GCACCACACCGUCCGGGCCCSMUCUN$_{16-23}$CUCUA | 57 |
| GAGNGN$_{15-22}$GARSGGGCCUACGACGGUGUUGUUCCGCUGC YCGUUCAUGGUUCCCMMUAUCUACUUCC<u>AUGUUAUAGAUCU CG</u>UGGAAGUAGCUUKKGGUUUGCAUGACCGRGGAGCUGCAC CACACCGUCCGGGCCCSMUCUN$_{16-23}$CUCUA | 58 |
| GAGNGN$_{15-22}$GARSGGGCCUACGGACGGUGUUGUUCCGCUGC YCGUUCAUGGUUCCCMMUAUCUACUUCC<u>AUCAGAGAGAGAG AGAGAUGUC</u>UGGAAGUAGCUUKKGGUUUGCAUGACCGRGGA GCUGCACCACACCGUCCGGGCCCSMUCUN$_{16-23}$CUCUA | 59 |
| GAGNGN$_{15-22}$GARSGGGCCUACGGACGGUGUUGUUCCGCUGC YCGUUCAUGGUUCCCMMUAUCUACUUCC<u>AUCAUGUGUAUAU AUGUAAUCCAUGGGGGAGGG</u>UUCUCUCGUCUUUGGAAGUAG CUUKKGGUUUGCAUGACCGRGGAGCUGCACCACACCGUCCG GGCCCSMUCUN$_{16-23}$CUCUA | 60 |
| GAGNGN$_{15-22}$GARSGGGCCUACGGACGGUGUUGUUCCGCUGC YCGUUCAUGGUUCCCMMUAUCUACUUCC<u>AUCAUCUUAUACA UCUCC</u>UUGGAAGUAGCUUKKGGUUUGCAUGACCGRGGAGCU GCACCACACCGUCCGGGCCCSMUCUN$_{16-23}$CUCUA | 61 |
| GCGUUAUUCGGUGUUUGAAGNGN$_{15-22}$GAAGGGGCCUACGGA CGGUGUUGUUCCGCUGCUCGUUCAUGGUUCCCCAUAUCUAC UUCCAUCAUGUUAUAGAUCUCGUCUUUGGAAGUAGCUUUGG GUUUGCAUGACCGAGGAGCUGCACCACACCGUCCGGGCCCG CUCUN$_{16-23}$CAUCCUAACACCUGCCAUUGU | 62 |

In accordance with the IUPAC nucleotide code, R represents A or G; S represents G or C; Y represents U or C; M represents A or C; W represents U or A; and K represents U or G.

A synthetic precursor molecule of the invention does not comprise a 100% identity to any wild type miRNA precursor molecule (e.g., does not comprise a 100% identity to MIR159, MIR156, MIR319, and the like). In some aspects, a synthetic precursor molecule of the invention does not comprise a 100% identity to 50, 100, 150, 200 or 250 contiguous nucleotides of any wild type miRNA precursor molecule.

The present invention provides a miRNA precursor into which any guide strand can be placed for expression in plants. Thus, the present invention provides synthetic precursor molecules comprising target-specific amiRNAs or miRNA guide strands that can be used in modulating the expression of a target gene or target polynucleotide. In some aspects, a miRNA guide strand of a synthetic miRNA precursor molecule of the invention can be about 60% to about 100% (e.g., 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or any value or range therein) complementary to a target gene or target polynucleotide (or fragment thereof) in a plant of interest. A miRNA guide strand of the invention forms a double stranded (ds) RNA molecule through complementary base pairing with a miRNA passenger strand. The miRNA passenger strand is designed to base pair with the miRNA guide strand such that the dsRNA formed comprises, consists essentially of, or consists of three mismatches with a first mismatch formed between the 5' most nucleotide U of the guide strand and the 3' most nucleotide of the passenger strand, the second single nucleotide mismatch formed six nucleotides (including the mismatched nucleotide) upstream (5') of the first mismatch and a third single nucleotide mismatch formed four nucleotides (including the mismatched nucleotide) upstream (5') of the second mismatch. In some embodiments, all three mismatches formed when the miRNA passenger strand and the miRNA guide strand base pair comprise, consist essentially of, or consist of a single base pair. In some embodiments, one of the three mismatches can comprise, consist essentially of, or consist of a length of 2 to 3 contiguous nucleotides. Accordingly, in some aspects, a miRNA passenger strand and a miRNA guide strand of the synthetic miRNA precursor molecule of the invention have about 70 to 90% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, or any value or range therein) complementarity to one another. In representative embodiments, a miRNA passenger strand and a miRNA guide strand of the synthetic miRNA precursor molecule of the invention have about 80 to 90% (e.g., 80%, 81%, 82%, 83%, 84%, 85%, 86%, 87%, 88%, 89%, 90%, or any value or range therein) complementarity to one another.

In some aspects, the length of a amiRNA (guide strand) can be about 17 to about 24 nucleotides in length (e.g., 17, 18, 19, 20, 21, 22, 23, 24 nucleotides in length, and/or any range therein).

In some aspects, a recombinant nucleic acid molecule comprises a nucleotide sequence encoding a synthetic miRNA precursor of the invention. In some aspects, the invention provides an expression cassette or vector comprising a nucleotide sequence encoding a synthetic miRNA precursor of the invention. In some aspects of the invention, the nucleotide sequence encoding a synthetic miRNA precursor of the invention can be RNA or DNA.

In some aspects, the nucleotide sequences and/or recombinant nucleic acid molecules of the invention can be operatively linked to one or more promoter sequences for expression in host cells (e.g., plant cells). Promoters useful with the invention include, but are not limited to, those that drive expression of a nucleotide sequence constitutively, those that drive expression when induced, and those that drive expression in a tissue- or developmentally-specific manner. These various types of promoters are known in the art.

The choice of promoter will vary depending on the temporal and spatial requirements for expression, and also depending on the host cell to be transformed. Thus, for example, expression of the nucleotide sequences of the invention can be in any plant and/or plant part, (e.g., in cells, in leaves, in stalks or stems, in ears, in inflorescences (e.g. spikes, panicles, cobs, etc.), in roots, seeds and/or seedlings, and the like). In many cases, however, protection against more than one type of pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Examples of constitutive promoters include, but are not limited to, cestrum virus promoter (cmp) (U.S. Pat. No. 7,166,770), the rice actin 1 promoter (Wang et al. (1992) Mol. Cell. Biol. 12:3399-3406; as well as U.S. Pat. No. 5,641,876), CaMV 35S promoter (Odell et al. (1985) Nature 313:810-812), CaMV 19S promoter (Lawton et al. (1987) Plant Mol. Biol. 9:315-324), nos promoter (Ebert et al. (1987) Proc. Natl. Acad. Sci USA 84:5745-5749), Adh promoter (Walker et al. (1987) Proc. Natl. Acad. Sci. USA 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. Plant Science 79: 87-94), maize (Christensen et al., 1989. Plant Molec. Biol. 12: 619-632), and arabidopsis (Norris et al. 1993. Plant Molec. Biol. 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (Mol. Gen. Genet. 231: 150-160 (1991)) can be easily modified for the expression of the nucleotide sequences of the invention and are particularly suitable for use in monocotyledonous hosts.

In some embodiments, tissue specific/tissue preferred promoters can be used. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, Plant Molec. Biol. 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) Seed Sci. Res. 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087, all incorporated by reference Additional examples of tissue-specific/tissue preferred promoters include, but are not limited to, the root-specific promoters RCc3 (Jeong et al. Plant Physiol. 153:185-197 (2010)) and RB7 (U.S. Pat. No. 5,459,252), the lectin promoter (Lindstrom et al. (1990) Der. Genet. 11:160-167; and Vodkin (1983) Prog. Clin. Biol. Res. 138:87-98), corn alcohol dehydrogenase 1 promoter (Dennis et al. (1984) Nucleic Acids Res. 12:3983-4000), 5-adenosyl-L-methionine synthetase (SAMS) (Vander Mijnsbrugge et al. (1996) Plant and Cell Physiology, 37(8):1108-1115), corn light harvesting complex promoter (Bansal et al. (1992) Proc. Natl. Acad. Sci. USA 89:3654-3658), corn heat shock protein promoter (O'Dell et al. (1985) EMBO J. 5:451-458; and Rochester et al. (1986) EMBO J 5:451-458), pea small subunit RuBP carboxylase promoter (Cashmore, "Nuclear genes encoding the small subunit of ribulose-1,5-bisphosphate carboxylase" pp. 29-39 In: Genetic Engineering of Plants (Hollaender ed., Plenum Press 1983; and Poulsen et al. (1986) Mol. Gen. Genet. 205:193-200), Ti plasmid mannopine synthase promoter (Langridge et al. (1989) Proc. Natl. Acad. Sci. USA 86:3219-3223), Ti plasmid nopaline synthase promoter (Langridge et al. (1989), supra), petunia chalcone isomerase promoter (van Tunen et al. (1988) EMBO J. 7:1257-1263), bean glycine rich protein 1 promoter (Keller et al. (1989) Genes Dev. 3:1639-1646), truncated CaMV 35S promoter (O'Dell et al. (1985) Nature 313:810-812), potato patatin promoter (Wenzler et al. (1989) Plant Mol. Biol. 13:347-354), root cell promoter (Yamamoto et al. (1990) Nucleic Acids Res. 18:7449), maize zein promoter (Kriz et al. (1987) Mol. Gen. Genet. 207:90-98; Langridge et al. (1983) Cell 34:1015-1022; Reina et al. (1990) Nucleic Acids Res. 18:6425; Reina et al. (1990) Nucleic Acids Res. 18:7449; and Wandelt et al. (1989) Nucleic Acids Res. 17:2354), globulin-1 promoter (Belanger et al. (1991) Genetics 129:863-872), a-tubulin cab promoter (Sullivan et al. (1989) Mol. Gen. Genet. 215:431-440), PEPCase promoter (Hudspeth & Grula (1989) Plant Mol. Biol. 12:579-589), R gene complex-associated promoters (Chandler et al. (1989) Plant Cell 1:1175-1183), and chalcone synthase promoters (Franken et al. (1991) EMBO J. 10:2605-2612). In some particular embodiments, the nucleotide sequences of the invention are operatively associated with a root-preferred promoter.

Particularly useful for seed-specific expression is the pea vicilin promoter (Czako et al. (1992) Mol. Gen. Genet. 235:33-40; as well as the seed-specific promoters disclosed in U.S. Pat. No. 5,625,136. Useful promoters for expression in mature leaves are those that are switched on at the onset of senescence, such as the SAG promoter from Arabidopsis (Gan et al. (1995) Science 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further aspects, the nucleotide sequences of the invention can be operatively associated with a promoter that is wound inducible or inducible by pest or pathogen infection (e.g., a nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded. Such promoters include, but are not limited to, those described by Stanford et al., *Mol. Gen. Genet.* 215:200-208 (1989), Xu et al. *Plant Molec. Biol.* 22:573-588 (1993), Logemann et al. *Plant Cell* 1:151-158 (1989), Rohrmeier and Lehle, *Plant Molec. Biol.* 22:783-792 (1993), Firek et al. *Plant Molec. Biol.* 22:129-142 (1993), Warner et al. *Plant J.* 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

As used herein, "expression cassette" means a nucleic acid molecule comprising a nucleotide sequence of interest (e.g., the nucleotide sequences encoding the synthetic miRNA precursor molecules of the invention), wherein said nucleotide sequence is operatively associated with at least a control sequence (e.g., a promoter). Thus, some embodiments of the invention provide expression cassettes designed to express the nucleotides sequences of the invention (e.g., the nucleotide sequences encoding the synthetic miRNA precursor molecules of the invention). In this manner, for example, one or more plant promoters operatively associated with one or more nucleotide sequences of the invention (e.g., SEQ ID NO:9 and/or SEQ ID NOs:18-62) are provided in expression cassettes for expression in an organism or cell thereof (e.g., a plant, plant part and/or plant cell).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of the invention can also include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, promoters, enhancers, introns, translation leader sequences, termination signals, and polyadenylation signal sequences.

For purposes of the invention, the regulatory sequences or regions can be native/analogous to the plant, plant part and/or plant cell and/or the regulatory sequences can be native/analogous to the other regulatory sequences. Alternatively, the regulatory sequences may be heterologous to the plant (and/or plant part and/or plant cell) and/or to each other (i.e., the regulatory sequences). Thus, for example, a promoter can be heterologous when it is operatively linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and/or polynucleotide) are substantially modified from their original form and/or genomic locus, and/or the promoter is not the native promoter for the operably linked polynucleotide.

A number of non-translated leader sequences derived from viruses are known to enhance gene expression. Specifically, leader sequences from Tobacco Mosaic Virus (TMV, the "w-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

An expression cassette of the invention also can include nucleotide sequences that encode other desired traits. Such desired traits can be other nucleotide sequences which confer nematode resistance, insect resistance, disease resistance, or which confer other agriculturally desirable traits, such as tolerance to abiotic stresses. Such nucleotide sequences can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853. In representative embodiments, a nucleic acid molecule, expression cassette or vector of the invention can comprise a transgene that confers resistance to one or more herbicides, optionally glyphosate-, sulfonylurea-, imidazolinione-, dicamba-, glufisinate-, phenoxy proprionic acid-, cycloshexome-, traizine-, benzonitrile-, and/or broxynil-resistance; a transgene that confers resistance to one or more pests, optionally bacterial-, fungal, gastropod-, insect-, nematode-, oomycete-, phytoplasma-, protozoa-, and/or viral-resistance, and/or a transgene that confers resistance to one or more diseases.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of plants and other organisms are well known in the art. Non-limiting examples of general classes of vectors include a viral vector including but not limited to an adenovirus vector, a retroviral vector, an adeno-associated viral vector, a plasmid vector, a phage vector, a phagemid vector, a cosmid, a fosmid, a bacteriophage, or an artificial chromosome. The selection of a vector will depend upon the preferred transformation technique and the target species for transformation. Accordingly, in further embodiments, a recombinant nucleic acid molecule of the invention can be comprised within a recombinant vector. The size of a vector can vary considerably depending on whether the vector comprises one or multiple expression cassettes (e.g., for molecular stacking). Thus, a vector size can range from about 3 kb to about 30 kb. Thus, in some embodiments, a vector is about 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, or any range therein, in size. In some particular embodiments, a vector can be about 3 kb to about 10 kb in size.

A large number of vectors known in the art may be used to manipulate nucleic acids, incorporate response elements and promoters into genes, etc. For example, the insertion of nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes). Vectors may be introduced into cells by any suitable method known in the art, including, but not limited to, transfection, electroporation, microinjection, transduction, cell fusion, DEAE dextran, calcium phosphate precipitation, lipofection (lysosome fusion), and use of a gene gun or nucleic acid vector transporter.

In some aspects, a method of modulating the expression of a target polynucleotide or a target gene in a plant or plant part is provided, the method comprising: introducing into said plant or plant part a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector to produce a transgenic plant or plant part, thereby modulating the expression of the target sequence in said transgenic plant or plant part.

In further aspects, a method of modulating the expression of a target polynucleotide or a target gene in a plant or plant part is provided, the method comprising: introducing into a plant cell a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector to produce a transgenic plant cell; and regenerating a plant or plant part from said plant cell, thereby modulating the expression of a target polynucleotide or a target gene in said plant or plant part.

In other aspects, a method of producing a transgenic plant or plant part having modulated expression of a target polynucleotide or target gene is provided, the method comprising: introducing into a plant or plant part a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector, thereby producing a transgenic plant or plant part having modulated expression of said target polynucleotide or target gene.

In further aspects, a method of producing a transgenic plant or plant part having modulated expression of a target polynucleotide or target gene is provided, the method comprising: introducing into said plant or plant part a synthetic miRNA precursor molecule of the invention, said miRNA precursor molecule comprising a guide sequence complementary to said target polynucleotide or target gene, optionally wherein the synthetic miRNA precursor molecule of the invention can be comprised in a recombinant nucleic acid, an expression cassette or a vector; and regenerating a plant or plant part from said plant cell, thereby producing a transgenic plant or plant part having modulated expression of said target polynucleotide or target gene.

In additional embodiments of the invention, a method of producing a transgenic plant cell is provided, said method comprising introducing into a plant cell a synthetic miRNA precursor molecule of the invention, said miRNA precursor molecule comprising a guide miRNA complementary to a target polynucleotide or a target gene in said plant cell, optionally wherein the synthetic miRNA precursor molecule of the invention can be comprised in a recombinant nucleic acid, an expression cassette or a vector; thereby producing a transgenic plant cell that can be regenerated into a transgenic plant or plant part having modulated (increased or decreased) expression of said target polynucleotide or target gene as compared to a plant or plant part regenerated from a plant cell that does not comprise said synthetic miRNA precursor molecule. Thus, in some aspects, the invention provides a transgenic plant or part thereof that is regenerated from the transgenic plant cell of the invention, wherein the transgenic plant or plant part has modulated (increased or decreased) expression of said target polynucleotide or target gene as compared to a plant or plant part regenerated from a plant cell that does not comprise said synthetic miRNA precursor molecule.

In some aspects, the expression of the target nucleic or target gene can be decreased compared to a control. In other aspects, the expression of the target nucleic or target gene can be increased compared to a control. A control can include, but is not limited to, a plant, plant part or plant cell that is not transformed with a synthetic miRNA precursor of the invention, or a control can be a plant, plant part or plant cell that is transformed with a synthetic miRNA precursor of the invention comprising a guide strand having no complementarity to said target gene or target polynucleotide (or no complementarity to any target gene or target polynucleotide) in said plant, plant part or plant cell. In some aspects, the control plant, plant part or plant cell can be the same species as the plant, plant part, or plant cell into which a synthetic miRNA precursor molecule of the invention (comprising a guide sequence complementary to said target polynucleotide or target gene) is introduced.

In some aspects, a transgenic plant, plant part or plant cell can comprise more than one (e.g., 2, 3, 4, 5, 6, 7, 8, 9, 10, etc.) synthetic miRNA precursor molecule of the invention.

"Introducing," in the context of a nucleotide sequence of interest (e.g., a nucleotide sequence encoding a synthetic miRNA precursor molecule of the invention), means presenting the nucleotide sequence of interest to the plant, plant part, and/or plant cell in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, for example, "introducing" can encompass transformation of an ancestor plant with a nucleotide sequence of interest followed by conventional breeding process to produce progeny comprising said nucleotide sequence of interest.

Transformation of a cell may be stable or transient. Thus, in some embodiments, a plant cell of the invention is stably transformed with a nucleotide sequence encoding a synthetic miRNA precursor molecule of the invention. In other embodiments, a plant of the invention is transiently transformed with a nucleotide sequence encoding a synthetic miRNA precursor molecule of the invention.

"Transient transformation" in the context of a polynucleotide means that a polynucleotide is introduced into the cell and does not integrate into the genome of the cell.

"Stable transformation" or "stably transformed," "stably introducing," or "stably introduced" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism or by quantitative reverse transcription and polymerase chain reaction (qRT-PCR). Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Methods of introducing a nucleic acid into a plant can also comprise in vivo modification of nucleic acids, methods for which are known in the art. For example, in vivo modification can be used to insert a nucleic acid comprising, e.g., a promoter sequence into the plant genome. In a further non-limiting example, in vivo modification can be used to modify the endogenous nucleic acid itself and/or a endogenous transcription and/or translation factor associated with the endogenous nucleic acid, such that the transcription and/or translation of said endogenous nucleic acid is altered, thereby altering the expression said endogenous nucleic acid and/or in the case of nucleic acids encoding polypeptides, the production of said polypeptide.

Exemplary methods of in vivo modification include zinc finger nuclease, CRISPR-Cas, TALEN, TILLING (Targeted Induced Local Lesions IN Genomes) and/or engineered meganuclease technology.

For example, suitable methods for in vivo modification include the techniques described in Urnov et al. *Nature Reviews* 11:636-646 (2010)); Gao et. al., *Plant J.* 61, 176 (2010); Li et al., *Nucleic Acids Res.* 39, 359 (2011); Miller et al. 29, 143-148 (2011); Christian et al. *Genetics* 186, 757-761 (2010)); Jiang et al. *Nat. Biotechnol.* 31, 233-239 (2013)); U.S. Pat. Nos. 7,897,372 and 8,021,867; U.S. Patent Publication No. 2011/0145940 and in International Patent Publication Nos. WO 2009/114321, WO 2009/134714 and WO 2010/079430; U.S. Pat. Nos. 8,795,965 and 8,771,945 For example, one or more transcription affector-like nucleases (TALEN) and/or one or more meganucleases may be used to incorporate an isolated nucleic acid comprising a promoter sequence of the invention into the plant genome. In representative embodiments, the method comprises cleaving the plant genome at a target site with a TALEN and/or a meganuclease and providing a nucleic acid that is homologous to at least a portion of the target site and further comprises a promoter sequence of the invention (optionally in operable association with a heterologous nucleotide sequence of interest), such that homologous recombination occurs and results in the insertion of the promoter sequence of the invention into the genome. Alternatively, in some embodiments, a CRISPR-Cas system can be used to specifically edit the plant genome so as to alter the expression of endogenous nucleic acids described herein. In some embodiments, a genetic modification may also be introduced using the technique of TILLING, which combines high-density mutagenesis with high-throughput screening methods. Methods for TILLING are well known in the art (McCallum, *Nature Biotechnol.* 18, 455-457, 2000, Stemple, *Nature Rev. Genet.* 5, 145-150, 2004).

As would be understood by the skilled artisan, the polynucleotides of the invention can be modified in vivo using the above described methods as well as any other method of in vivo modification known or later developed.

Thus, one or more nucleotide sequences encoding one or more synthetic miRNA precursor molecules of the invention (e.g., one or more of the nucleotide sequences of SEQ ID NO:9 and/or SEQ ID NOs:18-62) can be introduced into a cell by any method known to those of skill in the art. In some embodiments of the invention, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation-sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169).

The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877). Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

Likewise, the genetic properties engineered into the transgenic seeds and plants, plant parts, and/or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, in separate transformation events, or, for example, in plants, as part of a breeding protocol.

As used herein, the term "plant" may refer to any suitable plant, including, but not limited to, spermatophytes (e.g., angiosperms and gymnosperms) and embryophytes (e.g., bryophytes, ferns and fern allies). In some embodiments, a plant useful with this invention includes any monocot plant and/or any dicot plant.

Representative host plants include soybean (*Glycine max*), corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), tobacco (*Nicotiana tabacum*), potato (*Solanum tuberosum*), peanuts (*Arachis hypogaea*), cotton (*Gossypium hirsutum*), sweet potato (*Ipomoea batatas*), cassava (*Manihot esculenta*), coffee (*Coffea* ssp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), papaya (*Carica papaya*), cashew (*Anacardium occidental*), macadamia (*Macadamia integrifolia*), almond (*Prunus amygdalus*), sugar beets (*Beta vulgaris*), oats, barley, vegetables, ornamentals, and conifers.

Additional host plants of the invention are crop plants, for example, cereals and pulses, maize, wheat, potatoes, tapioca, rice, sorghum, millet, cassava, barley, pea, and other root, tuber, or seed crops or turf grasses. Important seed crops for the invention are oil-seed rape, sugar beet, maize, sunflower, soybean, and sorghum. Horticultural plants to which the invention may be applied may include lettuce, endive, and vegetable *brassica* including cabbage, broccoli, and cauliflower, and carnations, geraniums, petunias, and begonias. The invention may be applied to tobacco, cucurbits, carrot, strawberry, sunflower, tomato, pepper, *chrysanthemum*, poplar, *eucalyptus*, and pine. Optionally, plants of the invention include grain seeds, such as corn, wheat, barley, rice, sorghum, rye, etc. Optionally, plants of the invention include oil-seed plants. Oil seed plants include canola, cotton, soybean, safflower, sunflower, *brassica*, maize, alfalfa, palm, coconut, etc. Optionally, plants of the invention include leguminous plants. Leguminous plants include beans and peas. Beans include guar, locust bean, fenugreek, soybean, garden beans, cowpea, mung bean, lima bean, fava bean, lentils, chickpea, etc. Host plants useful in the invention are row crops and broadcast crops. Non-limiting examples of useful row crops are corn, soybeans, cotton, amaranth, vegetables, rice, sorghum, wheat, milo, barley, sunflower, durum, and oats. Non-limiting examples of useful broadcast crops are sunflower, millet, rice, sorghum, wheat, milo, barley, durum, and oats. Host plants useful in the invention are monocots and dicots. Non-limiting examples of useful monocots are rice, corn, wheat, palm trees, turf grasses, barley, and oats. Non-limiting examples of useful dicots are soybean, cotton, alfalfa, canola, flax, tomato, sugar beet, sunflower, potato, tobacco, corn, wheat, rice, lettuce, celery, cucumber, carrot, and cauliflower, grape, and turf grasses. Host plants useful in the invention include plants cultivated for aesthetic or olfactory benefits. Non-limiting examples include flowering plants, trees, grasses, shade plants, and flowering and non-flowering ornamental plants. Host plants useful in the invention include plants cultivated for nutritional value, fibers, wood, and industrial products.

In some particular embodiments, a plant of the invention includes, but is not limited to, a soybean plant, a sugar beet plant, a corn plant, a cotton plant, a canola plant, a sugar cane plant, a wheat plant, a rice plant or a turf grass plant.

In other embodiments, a plant cell of the invention includes, but is not limited to, a soybean cell, a sugar beet cell, a corn cell, a cotton cell, a canola cell, a sugar cane cell, a wheat cell, a rice cell or the cell of a turf grass.

As used herein, the term "plant part" includes but is not limited to embryos, pollen, ovules, seeds, leaves, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. Further, as used herein, "plant cell" refers to a structural and physiological unit of the plant, which comprises a cell wall and also may refer to a protoplast. A plant cell of the invention can be in the form of an isolated single cell or can be a cultured cell or can be a part of a higher-organized unit such as, for example, a plant tissue or a plant organ. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development. In some embodiments of the invention, a transgenic tissue culture or transgenic plant cell culture is provided, wherein the transgenic tissue or cell culture comprises a nucleic acid molecule/nucleotide sequence of the invention.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A further aspect of the invention provides transformed non-human host cells and transformed non-human organisms comprising the transformed non-human cells, wherein the transformed cells and transformed organisms comprise a synthetic miRNA precursor molecule of the invention. In some embodiments, the transformed non-human host cell includes but is not limited to a transformed fungal cell (e.g., a transformed yeast cell), a transformed insect cell, a transformed bacterial cell, and/or a transformed plant cell. Thus, in some embodiments, the transformed non-human organism comprising the transformed non-human host cell includes, but is not limited to, a transformed fungus, a transformed insect, a transformed bacterium, and/or a transformed plant.

In some aspects, the invention provides plants, plant parts, and/or plant cells produced by the methods of the invention. In representative embodiments, the invention provides a seed from a plant of the invention comprising in its genome a synthetic miRNA precursor molecule of the invention and a plant grown from said seed. Additional aspects of the invention include a product harvested from the plants and/or parts thereof of the invention, as well as a post-harvest product produced from said harvested product. A harvested product can be a whole plant or any plant part, as described herein, wherein said harvested product comprises a nucleotide sequence encoding at least one of the miRNA precursor molecules of the invention (e.g., SEQ ID NO:9 and/or SEQ ID NOs:18-62). Thus, in some embodiments, non-limiting examples of a harvested product include a seed, a fruit, a flower or part thereof (e.g., an anther, a stigma, and the like), a leaf, a stem, and the like. In other embodiments, a post-harvest product includes, but is not limited to, a flour, meal, oil, starch, cereal, and the like produced from a harvested seed of the invention, wherein said seed comprises in its genome a nucleotide sequence encoding at least one of the miRNA precursor molecules of the invention.

In some embodiments, the invention further provides a plant crop comprising a plurality of transgenic plants of the invention planted together in, for example, an agricultural field, a golf course, a residential lawn, a road side, an athletic field, and/or a recreational field.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1: Control miRNA Precursor Constructs

The native miR156 guide strand was used to show precursor efficacy. miR156 has several target genes in the maize genome including teosinte glume architecture 1 (tga1), a gene responsible for a major QTL in the evolution of maize from teosinte and sp19 (*SQUAMOSA* PROMOTER BINDING PROTEIN (SBP)-box family of transcription factors). Overexpression of miR156 in maize has been shown to produce a grass-like phenotype (see, Chuck et al. *Nature Genetics* 39, 544-549 (2007)). Expression of miR156 also results in decreased expression of miR172 expression (Id.). Thus, these three target genes were used to assess efficacy of the synthetic precursors of the invention in plants.

As a positive control, the native miRNA precursor zma-MIR159a was modified, replacing the native miR159 guide sequence with miR156 to produce zma-MIR159a-miR156 (FIG. 2). miRNA precursor zma-MIR159a is shown in FIG. 1 with its endogenous or native guide strand. As a further control, the native miR159 guide sequence of the MIR159a precursor was replaced with a scrambled miR156 sequence.

When expressed in plants, zma-MIR159a-miR156 results in an increase in miR156 expression, decreased TGA1 and miR172 transcripts, decreased miR172 expression and the grass-like phenotype (FIG. 3 and FIG. 4A-4C). The severity phenotype observed was correlated with miR156 expression level ($p<0.01$).

Example 2: Development of Synthetic Precursor Constructs

Analyzing native miRNA precursors provided the inventors with substantial information from which synthetic miRNA precursors could be developed.

Loop to base mechanism of DCL-1 processing was chosen for the synthetic precursors of this invention. Thus, in general, a synthetic miRNA precursor of the invention comprises (5' to 3') a 5' base sequence, followed by a passenger strand of the amiRNA/amiRNA* duplex and then a further strand of amiRNA* side of the amiRNA/amiRNA* duplex, a stem-loop sequence, the complementary strand of the further strand of amiRNA* side of the amiRNA/amiRNA* duplex, a guide strand (amiRNA) of the amiRNA/amiRNA* duplex (complementary to the passenger strand) and then a 3' base sequence. Notably, the 5' and 3' base sequences in the synthetic miRNA precursors of the invention can be absent or present without affecting DCL-1 processing.

For initial recognition by DCL1 two symmetric mismatches (mismatches having an equal number of nucleotides mismatched on both sides of the duplex) following the stem loop structure of the miRNA precursor were included in the synthetic miRNA precursor construct. Further, the duplex sequence 5' of the two symmetrical mismatches was constructed to have about 6 to 8 mismatches or bulges and the passenger/guide duplex was constructed to have three single nucleotide mismatches. The structure of the synthetic precursors of the invention is provided in the nucleotide sequence of SEQ ID NO:9, set forth below.

$N_{0-50}gNgN_{15-22}$ga[a/g][g/c]gggccuacggacgguguu-guuccgcugc[u/c]cguucaugguuccc [c/a] [a/c]uauc uacuuc-ca$N_{10-50}$uggaaguagcuu[u/g][g/u]gguuugcaugaccg[a/g] ggagcugcaccac accguccgggccc [g/c][c/a]ucu$N_{16-23}$c $N_{0-50}$ (SEQ ID NO:9).

Example 3: Efficacy of the Synthetic Precursors

The efficacy of a synthetic precursor miRNA was tested in maize using miR156 as the guide strand to target teosinte glume architecture 1 (tga1) as follows.

A synthetic miRNA precursor having the nucleotide sequence of: gcgttatteggtgtagaagegtgctcattatctcctgtct-gaaggggcctacggacggtgttgttccgctgctcgttcatggaccccatat ctacttccatcatgttatagatacgtattggaagtagattgggtagcatgaccgag-gagctgcaccacaccgtccgggcccgctctg acagaagagagtgagcacg-catcctaacacctgccattgt (SEQ ID NO:63) was constructed (dp0019) (which is the nucleotide sequence of SEQ ID NO:62 comprising miR156 as the experimental guide strand).

A binary base vector was used as basic backbone for delivery of the synthetic miRNA precursors using the 6-phosphomannose isomerase (PMI) selection feature for maize transfoiuiation. The basic cassette for expressing synthetic all the miRNA precursors contains eNOS-01as Enhancer, the promoter was prZmUbi158-05 (which has the first intron of the ubiquitin sequence) for driving synthetic precursor (Stem Loop), and tZmUbi158-02 as Terminator Recombinant DNA procedure followed procedures known in the art, for example, the dP0019.miR156-01 was synthesized by GenScript Company by introducing HindIII at the 5' end and RsrII at the 3' end. It was digested with HindIII/RsrII and then cloned into a binary base vector (HindIII/RsrII), the construct was digested and the 14137 bp fragment purified. Positive clones were verified with colony PCR. Positive clones were verified with ApaLI digestion. All cloning junctions were configured by sequencing with no error.

Maize plants were transformed with various constructs include a construct comprising SEQ ID NO:63 and control constructs as described above. Transformed maize callus was selected by resistance to mannose by PMI gene. A primary and secondary TaqMan assay was used to checking copy numbers in the seedlings. All the single copy events were moved forwarded for phenotypic observation and molecular characterization.

In addition to an assessment of the grass-like phenotype in the transgenic plants, the expression of three genes was measured. Wild type plants were used as a control with the expression of the target genes in the wild type set at 100%. Results from the phenotype assessment are shown in FIGS. 5A-5D and analysis of expression of the three target genes are shown in Table 2.

TABLE 2

Summary of the effect of expression of synthetic precursor dp0019 in maize

| | Target Genes Suppression (%) | | | | | |
|---|---|---|---|---|---|---|
| | Zma-MIR172 | | TGA1 | | SPL9 | |
| Plants | Average | STDEV | Average | STDEV | Average | STDEV |
| dp0019 (SEQ ID NO: 63) | 70.79% | 11.35% | 33.82% | 14.64% | 48.40% | 24.46% |
| WT | 0.00% | 0.00% | 0.00% | 0.00% | 0.00% | 0.00% |

Thus, transformation of maize plants with the synthetic precursor dp0019 comprising the miR156 guide strand produced the same grass-like phenotype (FIG. 5C) and had the same suppressive effect on tga1, sp19 and miR172 expression as the endogenous miRNA precursor zma-pre-MIR159a modified to comprise miR156 (zma-MIR159a-miR156, FIG. 2) when overexpressed in maize plants. This shows that that the synthetic miRNA precursor of the present invention is processed efficiently by DCL1 in plants and is therefore functional as a miRNA precursor in plants.

As exemplified by synthetic precursor dp0019, the rational design of the synthetic precursors of the invention provided herein can be used to construct a variety of miRNA precursors for the delivery of any guide miRNA targeting any gene of interest in a plant.

Example 4: Synthetic miRNA Precursor Molecules for Gene Silencing in Maize

A set of 21nt siRNA sequences were selected from the Zea mays DNA mismatch repair protein (MSH1) sequence (GenBank Accession No: NM_001112428.1). Each of the siRNAs was embedded into dp0019 in single or tandem multiple manors to generate a series of constructs: 22389, 22391, 22393, 22394, 22402 and 22404.

The constructs were transformed into maize producing a large number of transformants. After examination of T-DNA copy number, qRT-PCR analysis of target gene mRNA transcript and generated siRNA were carried out. Positive phenotypic events were selected for further characterization.

Figure 6:
FIG. 6 shows transgenic maize exhibiting mismatch repair protein (MSH1) gene silencing as demonstrated by leaf striping and pale color.

As FIG. 6 demonstrates, the white stripe and pale color of the leaves of the transgenic maize shows that the nuclear mismatch repairing gene (MSH1) had been silenced leading to a malfunctioning of the plastids.

Figure 7:
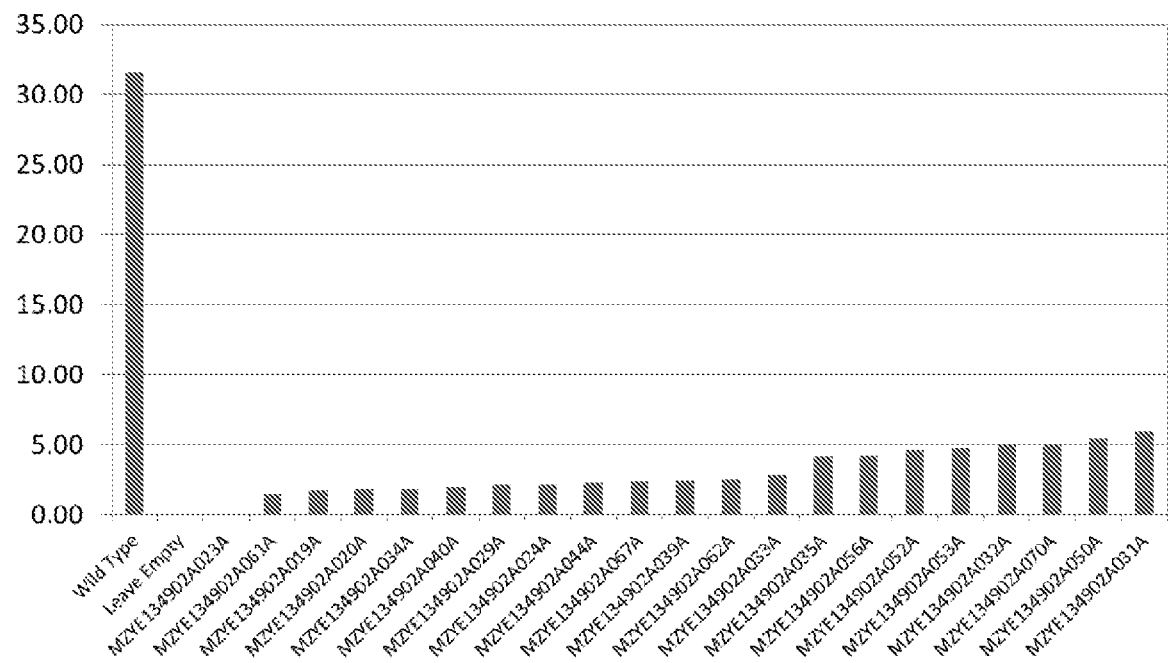
FIG. 7 shows MSH1 expression levels and gene silencing in transgenic maize using qRT-PCR analysis.

FIG. 7 provides the results of a qRT-PCR analysis using construct 22404, the results showing a very high level of target gene silencing, reaching as much as 100% silencing in one event.

Example 5: Synthetic miRNA Precursor Molecules for Gene Silencing in Soybean

A set of siRNA sequences were selected from the Glycine max DNA mismatch repair protein (MSH1) sequence (GenBank Accession No: NM_001251288). Each of the siRNAs was embedded into dp0019 in single or tandem multiple manors to generate a series of constructs: 2446, 22449, 22450, 22451, 22472 and 22473.

The constructs were transformed into soybean producing a large number of transformants. After examination of T-DNA copy number, qRT-PCR analysis of target gene mRNA transcript and generated siRNA were carried out. Positive phenotypic events were selected for further characterization.

Figure 8:
FIG. 8 shows transgenic soybean exhibiting MSH1 gene silencing as demonstrated by the bleached leaf phenotype.

Similar to maize, plants having bleached or white stripped leave were obtained, showing that the nuclear mismatch repairing gene (MSH1) had been silenced leading to a malfunctioning of the plastids. (FIG. 8).

Figure 9:
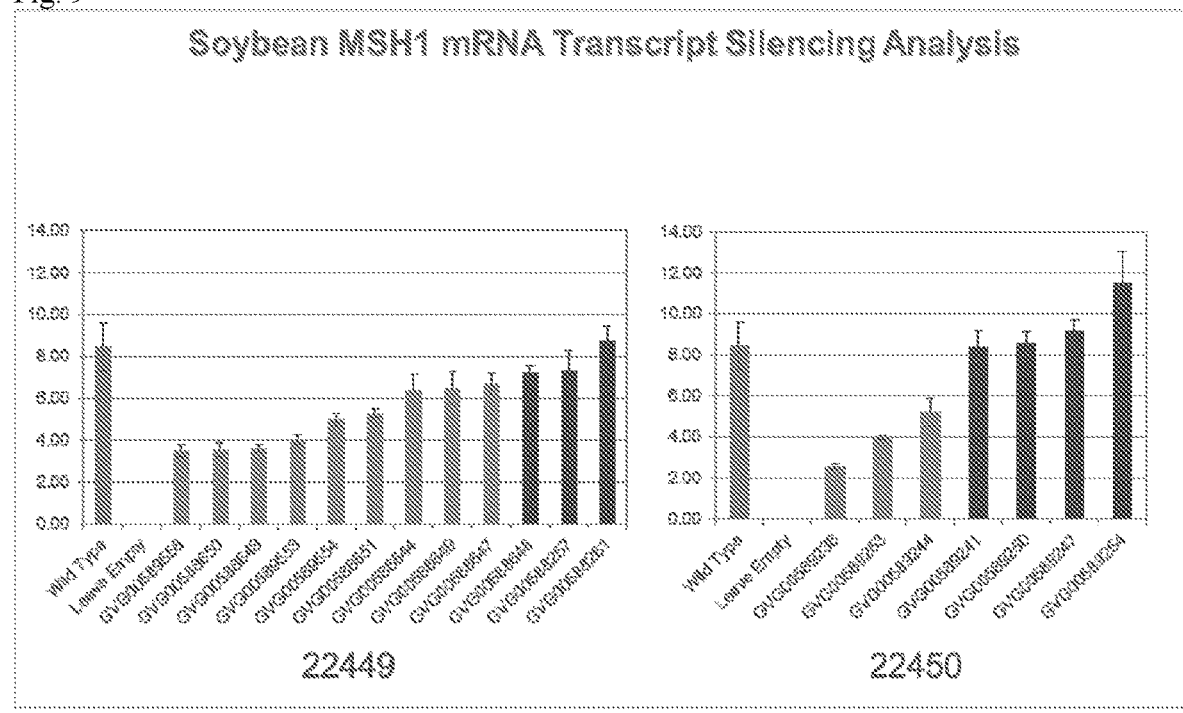
FIG. 9 shows MSH1 expression levels and gene silencing in transgenic soybean using qRT-PCR analysis.

In addition, qRT-PCR analysis confirmed MSH1 silencing in the transgenic soybean plants (FIG. 9). Even though there were some variation, the data provided evidence that dp0019 works well in dicot soybean plants.

Example 6: Synthetic miRNA Precursor Molecules for Gene Silencing in Rice

A set of siRNA sequences were selected from the Oryza sativa DNA mismatch repair protein (MSH1) sequence (GenBank Accession No: NP_001053261). Each of the siRNAs was embedded into dp0019 in single or tandem multiple manors to generate a series of constructs: 22624, 22643, 22644, The constructs were transformed into rice producing a large number of transformants. After examination of T-DNA copy number, qRT-PCR analysis of target gene mRNA transcript and generated siRNA were carried out. Positive phenotypic events were selected for further characterization.

Figure 10A:
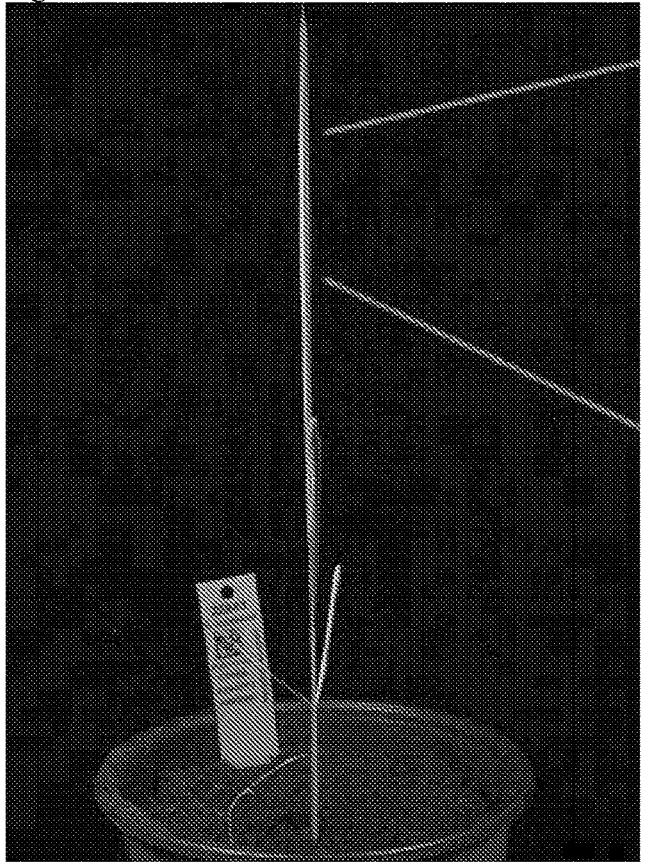
FIGS. 10A-10B show transgenic rice exhibiting MSH1 gene silencing as demonstrated by the white sectoring phenotype.
Figure 10B:
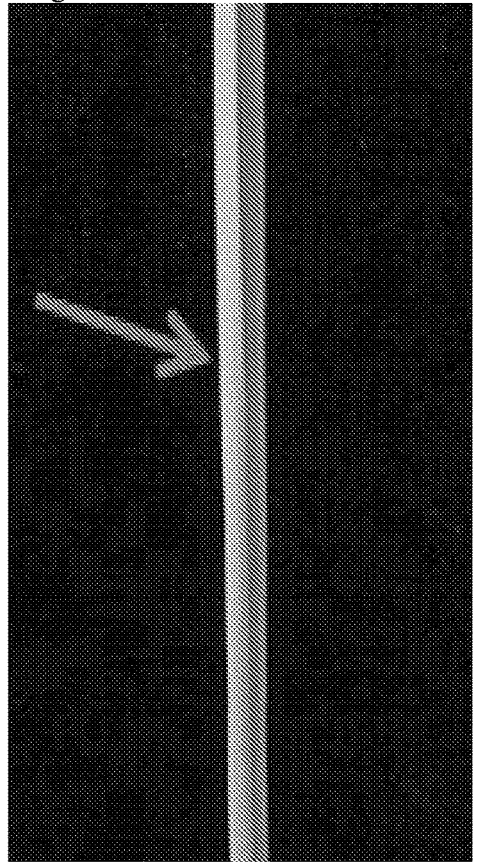

As seen in maize and soybean, plants having bleached or white stripped leave were obtained, showing that the nuclear mismatch repairing gene (MSH1) had been silenced leading to a malfunctioning of the plastids. (FIG. 10A-10B).

Figure 11:
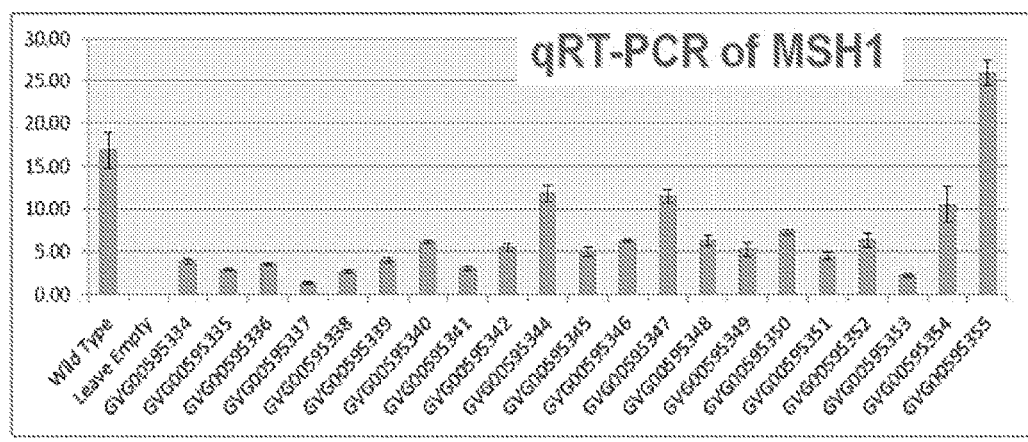
FIG. 11 shows MSH1 expression levels and gene silencing in transgenic rice by qRT-PCR analysis.

In addition, qRT-PCR analysis confirmed MSH1 silencing in the transgenic rice plants (FIG. 11). Even though there were some variation, the data provided evidence that dp0019 works well in the rice plants.

Example 6: Synthetic miRNA Precursor Molecules and Virus Induced Gene Silencing (VIGS) in Maize VIGS delivery of a genes of interest (GOI) has been shown to be an efficacious method for delivery of nucleic acid constructs. However, as far as these inventors are aware, delivery of a microRNA precursor to a plant via VIGS has not yet been demonstrated. This example shows that the synthetic miRNA precursors of the invention (e.g., dp0019) work well in a VIGS system.

A set of siRNA sequences were selected from the Zea mays phytoene desaturase (PD) sequence (GenBank Accession No: L39266.1). Each of the siRNAs was embedded into dp0019 in single or tandem multiple manors, which were inserted into BMV viral vectors to generate two constructs, 22897 and 22900.

Maize plantlets were inoculated with the viral vectors comprising dp0019 having the embedded siRNA sequences. One to two weeks following inoculation, qRT-PCR analysis of target gene mRNA transcript and generated siRNA were carried out.

Figure 12:
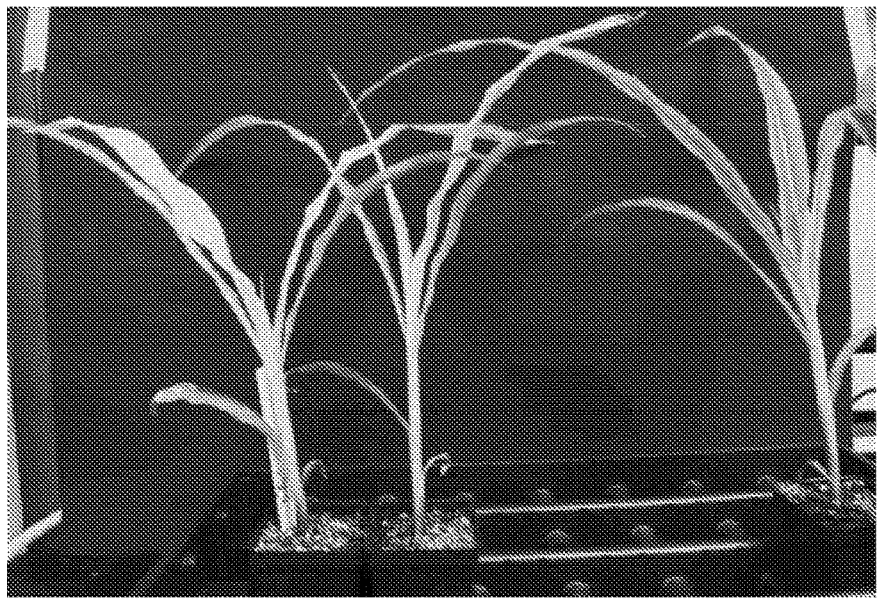
FIG. 12 shows transgenic corn exhibiting phytoene desaturase (PDs) gene silencing as demonstrated by the white sectoring phenotype. The photo was taken about 15 days after infiltrating the miRNA PDS (construct 22900) into the maize leaves.

As seen for maize, soybean and rice in Examples 4, 5 and 6, above, respectively, plants having a bleach leaf phenotype were obtained, demonstrating that the target PD gene has been silenced in the inoculated maize plants (FIG. 12). The plants were abraded with sandpaper prior to inoculation.

The foregoing is illustrative of the invention, and is not to be construed as limiting thereof. The invention is defined by the following claims, with equivalents of the claims to be included therein.

The invention claimed is:

1. A synthetic miRNA precursor molecule, wherein the sequence of the synthetic miRNA precursor molecule is SEQ ID NO. 63.

* * * * *